(12) United States Patent
Yim

(10) Patent No.: US 11,950,805 B2
(45) Date of Patent: Apr. 9, 2024

(54) SHARP TURNING STEERABLE NEEDLE

(71) Applicant: THE TRUSTEES OF THE UNIVERSITY OF PENNSYLVANIA, Philadelphia, PA (US)

(72) Inventor: Mark Yim, St. Davids, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 18/191,286

(22) Filed: Mar. 28, 2023

(65) Prior Publication Data
US 2023/0380863 A1     Nov. 30, 2023

Related U.S. Application Data

(63) Continuation of application No. 16/339,566, filed as application No. PCT/US2017/055327 on Oct. 5, 2017, now Pat. No. 11,648,031.

(60) Provisional application No. 62/404,394, filed on Oct. 5, 2016.

(51) Int. Cl.
| | |
|---|---|
| *A61B 17/34* | (2006.01) |
| *A61M 25/00* | (2006.01) |
| *A61M 25/01* | (2006.01) |
| *A61N 5/10* | (2006.01) |

(52) U.S. Cl.
CPC ..... *A61B 17/3421* (2013.01); *A61M 25/0084* (2013.01); *A61M 25/0127* (2013.01); *A61N 5/1007* (2013.01); *A61B 2017/3454* (2013.01); *A61M 2025/0092* (2013.01); *A61N 2005/1024* (2013.01)

(58) Field of Classification Search
CPC ............ A61B 17/3421; A61B 17/3478; A61B 17/3417; A61B 2017/3454; A61B 2017/003; A61B 10/04; A61B 2010/045; A61M 25/0084; A61M 25/0127; A61M 2025/0092; A61N 5/1007; A61N 2005/1024

See application file for complete search history.

(56) References Cited

U.S. PATENT DOCUMENTS

| | | | |
|---|---|---|---|
| 5,318,528 | A | 6/1994 | Heaven et al. |
| 5,792,110 | A | 8/1998 | Cunningham |
| 5,911,701 | A | 6/1999 | Miller et al. |
| 5,938,635 | A | 8/1999 | Kuhle |
| 6,572,593 | B1 | 6/2003 | Daum |
| 6,592,559 | B1 | 7/2003 | Pakter et al. |
| 7,354,033 | B1 | 4/2008 | Murphey et al. |

(Continued)

FOREIGN PATENT DOCUMENTS

WO     2015/153174 A1     10/2015

OTHER PUBLICATIONS

Majewicz et al., "Evaluation of robotic needle steering in ex vivo tissue", Proc. IEEE Int. Conf. Robotics and Automation, May 2010, pp. 2068-2073.

(Continued)

*Primary Examiner* — Devin B Henson
(74) *Attorney, Agent, or Firm* — BakerHostetler

(57) ABSTRACT

Disclosed are steerable needles having a shaft that can be controllably buckled, a steering head positioned at a distal end of the shaft, a transmission for controlling the orientation of the steering head, and a base at the end of the shaft, the base optionally comprising a controller for controlling the transmission. Also disclosed are methods of using the disclosed steerable needles.

14 Claims, 14 Drawing Sheets

(56) References Cited

U.S. PATENT DOCUMENTS

| | | |
|---|---|---|
| 7,822,458 B2 | 10/2010 | Webster, III |
| 11,207,500 B2 | 12/2021 | Su et al. |
| 2004/0133168 A1 | 7/2004 | Salcudean |
| 2006/0167416 A1 | 7/2006 | Mathis et al. |
| 2007/0167868 A1 | 7/2007 | Sauer |
| 2008/0308523 A1 | 12/2008 | Krulevitch et al. |
| 2012/0136381 A1 | 5/2012 | Morrison et al. |
| 2012/0191090 A1 | 7/2012 | Sugahara et al. |
| 2013/0123662 A1 | 5/2013 | Hipp |
| 2014/0276051 A1 | 9/2014 | Hoffman |
| 2014/0276586 A1 | 9/2014 | Swaney et al. |

OTHER PUBLICATIONS

Reed et al., "Robot-assisted needle steering," IEEE Robot. Autom. Mag., Dec. 2011, vol. 18, No. 4, pp. 35-46.

Swaney et al., "A Flexure-Based Steerable Needle: High Curvature With Reduced Tissue Damage", IEEE Transactions On Biomedical Engineering, Apr. 2013, vol. 60, No. 4, pp. 906-909.

Yan Nai et al., "Steerable Mechanical Joint for High Load Transmission in Minimally Invasive Instruments." ASME. J. Med. Devices, 2011, vol. 5, No. 3, pp. 1-6.

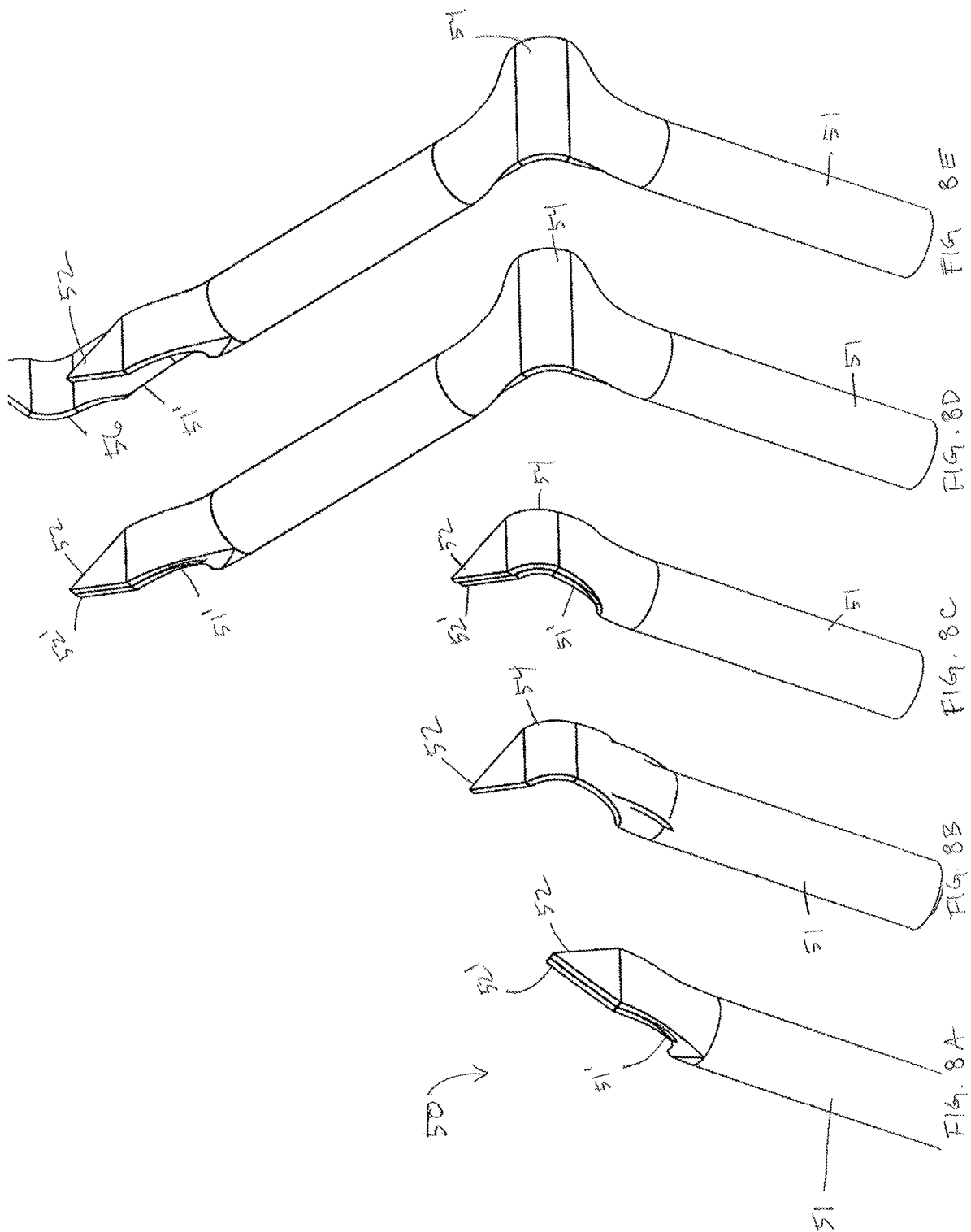

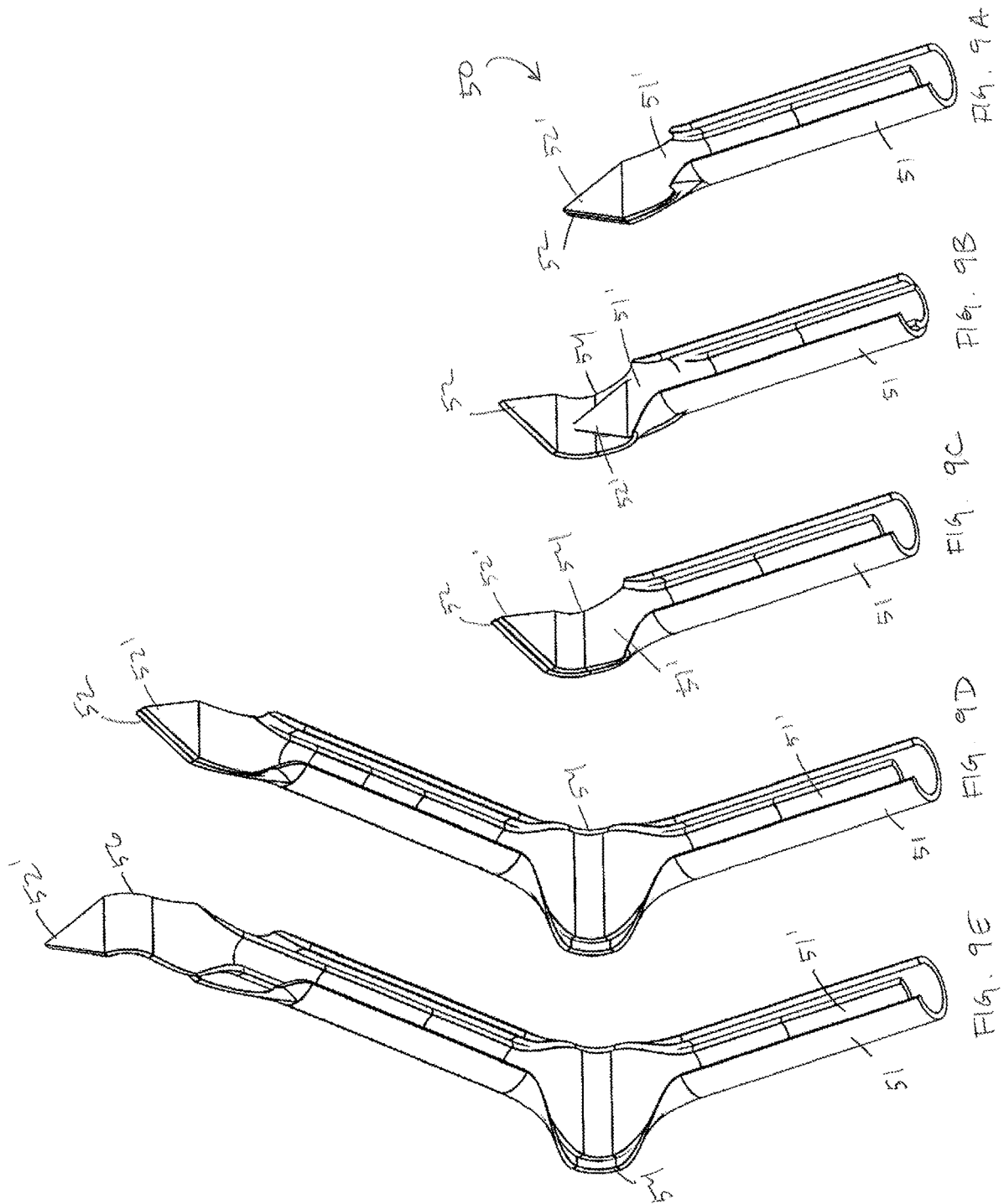

SHARP TURNING STEERABLE NEEDLE

CROSS REFERENCE TO RELATED APPLICATION

The present application claims priority to and the benefit of U.S. patent application Ser. No. 16/339,566, "Sharp Turning Steerable Needle" (filed Apr. 4, 2019), which claims priority to and the benefit of PCT application no. PCT/US2017/055327, "Sharp Turning Steerable Needle" (filed Oct. 5, 2017), which claims priority to and the benefit of U.S. patent application No. 62/404,394, "Sharp Turning Steerable Needle" (filed Oct. 5, 2016), the entirety of which applications are incorporated herein by reference for any and all purposes.

TECHNICAL FIELD

The present invention relates to sharp turning steerable needles, such as those for use in creating and following a path in tissue for diagnosis and treatment of patients.

BACKGROUND

Accurate and precise needle insertion is an important aspect of many types of medical diagnoses and treatments. The anatomy of different subjects, however, presents obstacles and challenges for accurate and precise needle insertion. To reach certain locations, needles must circumnavigate bones and precise insertion must account for differing reaction forces due to tissue variation, deflection, dislocation, or deformation.

Examples of medical treatments requiring accurate and precise needle insertion include, e.g., treatment of various cancers and intracranial hemorrhage, and diagnostic techniques such as biopsies of suspect tissue. To treat prostate cancer by transperineal brachytherapy, a needle is used to precisely implant radioactive seeds in the prostate. Thermal ablation is another technique relying on the use of needles for targeted treatment. Intracranial hemorrhages are treated by drilling burr holes in the skull and administering drugs with rigid needles, which requires the burr holes to be larger than otherwise necessary.

While steerable medical devices are known due to the use of steerable catheters, the capabilities of available steerable needles are significantly limited. Steerable catheters, which are typically much greater in diameter than needles, travel through fluid or air. Therefore, catheters are not subjected to the various reaction forces encountered by needles as they pass through tissue. The larger diameter of steerable catheters also allows for greater flexibility in design. Table 1 below highlights several of the differences between catheters and needles.

TABLE 1

Comparison of catheter and needle characteristics.

| | Catheters | Needles |
|---|---|---|
| Scale/Size | ca. 3-10 mm in diameter | ca. 0.5-3.0 mm in diameter |
| Length | 50-200 cm | 5-10 cm |
| Medium | Fluid/air | Soft-tissue/bone |
| Applications | Vascular examination, cardiac, urinary, etc. | Lung/kidney/liver biopsy/ablations and targeted drug delivery |
| Design | Flexible segments that can be steered with cables attached to tip | Single metal cylinder or rod |
| Guidance | Fluoroscopy, ultrasound | CT, fluoroscopy, ultrasound |

While both are capable of distal tip steering, catheters pass through channels within the body, and are therefore designed to steer in free space or fluid-filled conduits. Steerable needles, on the other hand, are designed to maneuver through tissue. To alter direction, steerable elements must be pre-curved when retracted and deployed along a curved path into tissue or an organ or else use the reaction forces at the tip of the needle for steering.

Another difference between steerable needles and catheters besides size is the attainable radius of curvature. Although catheters have much larger diameters, mechanisms can be more sophisticated that enable sharper curvatures (e.g., 1 cm) whereas steerable needles have limited flexibility. In order to maintain enough stiffness to move into the flesh in a controlled fashion, needles must maintain a minimum stiffness.

Steerable needle technology has the potential to change the way many surgeries are performed. The post-operative procedures after needle-based surgery consist of simply applying a bandage. Even so-called "minimally invasive" laparoscopic surgeries with small ports still need to have the ports stitched closed. Currently, straight needles are commonly used, but the straight needles can only be used in areas accessible by straight lines which limits them to places that are not blocked by important organs or bones.

At present, physicians attempt to steer standard needles by bending the part of the needle that is partially or fully outside the body so that it takes a curved trajectory when inserted. These curved needles, however, are limited to a fixed curvature and can only be used when simple geometry dictates its use (e.g., avoiding one sensitive region or obstacle).

Steerable needles could drive around multiple sensitive areas and obstacles or be adjusted in real time as the operation proceeds. In addition, there is the potential for a wider variety of capabilities. Since the needle is steerable, the needle could be used for catheter-like operations (e.g., transurethral resections of the prostate (TURP)) that include the removal of tissue. Another potential use for a steerable needle is for brain clot reduction and treating intracranial hemorrhage.

Radio Frequency Ablation (RFA) is used to do a variety of things. One of them is the treatment of cancerous tumors including liver, kidney, adrenal gland, bone, lung and breast as well as soft tissue debulking and pain palliation. RFA for cancerous tumors in the liver has been extensively used. Traditional methods are usually limited to tumors smaller than 5 cm as larger tumors would require more than a dozen needle insertions. There are several commercial devices which deploy an array of tines to ablate a larger spherical volume (e.g., 5 cm). For example, the Boston Scientific RF 3000 deploys a set of about 10 tines that curve out like an umbrella. The RITA Medical System Starburst XL has 9 tines that fan out like a Christmas tree. A needle that can achieve an arbitrary path can affect a volume of arbitrary shape and size by moving the RFA transducer along the path over time.

Steerable needles have been receiving a lot of attention from the research community due to advantages listed above. Some of the more promising work includes flexible needles with asymmetric (e.g., bevel-tip) devices, such as those disclosed in U.S. Pat. No. 7,822,458.

Asymmetric devices can create curving paths where the bevel tip causes the path of the needle to curve as it penetrates the tissue and can also create straight paths in tissue (by twisting while translating the bevel tip to form a helical path). These devices, however, are limited to creating paths with large curvatures. Such asymmetric devices have a minimum turning radius typically in the range of several inches or more. The amount of curvature available to asymmetric devices will also vary in shape depending on the stiffness of the tissue. As of 2011, the record for the tightest curve experimentally achieved was a radius of 1.5 cm in artificial tissue and 3.4 cm in the liver. See A. Majewicz, T. R. Wedlick, K. B. Reed, and A. M. Okamura, "Evaluation of robotic needle steering in ex vivo tissue," in Proc. IEEE Int. Conf. Robotics and Automation, May 2010, pp. 2068-2073.

U.S. Pat. No. 5,938,635 and U.S. Patent Application Publication No. 2004/0133168 highlight ways of steering within tissue using concentric pre-bent needles and "airfoil" needle shapes. These designs make use of specialized cutting surfaces to direct the orientation of a medical device.

U.S. Pat. No. 5,938,635 discloses a needle comprising a shaft, a tip which is flared in dimension with respect to the diameter of the shaft, and a longitudinal bevel which is imposed on the tip. The flared tip of the needle causes it to travel in an arc as the needle is pushed through tissue. Linear trajectories can be achieved by continuous rotation of the needle about its long axis or by stepwise rotations of the needle about its long axis as it is advanced into the tissue.

U.S. Patent Application Publication No. 2007/0167868 and U.S. Pat. No. 5,318,528 show two strategies for changing the orientation and curvature of tissue harvesting and surgical devices in free space.

U.S. Pat. Nos. 5,792,110; 6,592,559; and 6,572,593 show devices that use concentric compliant cylinders to change the orientation of the tip of a needle. Distal tip manipulation is achieved with a variety of strategies: bending the cannula with a pre-bent stylet, deploying a pre-bent stylet from a straight rigid cannula, and bending a stylet with a feature in the cannula lumen.

Examples of three steerable needles in use on the market today are the COOK Pakter Curved Needle Set, the COOK Osteo-Site Bone Access Products and the PneumRx Seeker Biopsy Needle, as disclosed in U.S. Patent Application Publication No. 2006/0167416. The Pakter and Osteo-Site products both employ pre-bent needles in concentric rigid cannulae. The Pakter and Osteo-Site products implement distal-tip needle steering to access the center of damaged vertebrae and spinal disks.

The Seeker needle mechanism disclosed in U.S. Patent Application Publication No. 2006/0167416 consists of a pivoting handle on the proximal end of the needle that is attached to its distal tip via four small steel bands. The radiologist can cause the needle to take a curved shape by manipulating the handle or joystick with his/her thumb. However, this device lacks accurate controllability, in particular, when it is already partially inserted into the body. Further, there is no locking mechanism to hold a particular curvature.

U.S. Patent Application Publication No. 2004/0133168 to Salcudean et al. discloses a robotic device that enables multiple needle curvatures to be achieved by employing a stylet that is longer than the cannula so that up to 2 cm of the stylet tip (with a mild curve) can be selectively exposed. The extended curve essentially acts as an adjustable bevel on the tip of the needle. Motors provide actuation for the rotation and extension of the stylet with respect to the cannula. The steering direction is selected by rotating the stylet and the steering rate is selected by extending the stylet and exposing the curve. By withdrawing the stylet, the stiffer cannula straightens out the curve and the needle becomes approximately straight. A miniature two-axis analog joystick is mounted on the shaft of the device facing opposite the insertion direction so that the physician can firmly hold the device in his or their palm and manipulate the joystick with the thumb. This system also requires a thin flexible needle that can bend so that the entire shaft can follow behind the steering tip. Although the hand held device improves the controllability, it would be difficult for a physician to hold for a long period of time.

There are fundamental problems with the needle steering strategies that have been developed to date. In particular, relying on knowledge of the material properties has obvious limitations. Material properties within tissue will be inhomogeneous, varying with patients as well as across tissue layers. Tissue properties may also change from the time of the initial diagnosis to the operation. Many of the research projects offer the potential for steering around anatomic structures; however, a major problem is that once the needle tip is placed at the desired point, it cannot be easily repositioned to a nearby point. Instead of steering the entire needle length, it would be desirable to be able to insert the needle along a straight trajectory and then have a mechanism for repositioning the distal tip of the needle. Such a mechanism would be useful for targeting multiple points in a volume or for directing the needle tip around obstacles when a straight-line trajectory cannot be taken.

One of the major challenges in designing steerable needles is that the stiffness in the flexible needle needs to be strong enough to penetrate the tissue without buckling yet flexible enough that it will curve in the tissue (ideally with small radius). In actual use, the flexible needle approaches (e.g. asymmetric (bevel-tip) devices) need to adjust a variety of properties to adjust for the tissue stiffness including the stiffness of the needle, the angle of any bevel, and the angle of any prebend (kink or curve bias). See, e.g., Philip Swaney, Jessica Burgner, Hunter B. Gilbert, and Robert Webster, "A Flexure-Based Steerable Needle: High Curvature With Reduced Tissue Damage" IEEE Transactions On Biomedical Engineering Vol. 60, No. 4, April 2013. This can be problematic as typically a needle must penetrate a variety of tissues, which will often vary especially if the tissue is tumorous.

A survey paper (K. Reed, A. Majewicz, V. Kallem, R. Alterovitz, K. Goldberg, N. Cowan, and A. Okamura, "Robot-assisted needle steering," IEEE Robot. Autom. Mag., vol. 18, no. 4, pp. 35-46, December 2011) summarizes many years of research in steerable needles using asymmetric-tip needles and concludes that there are four areas of development required to achieve application in the real world. These areas include:

1) mechanics-based modeling—understanding the needle/tissue interaction is important for asymmetric tip needles;
2) planning in 3D with uncertainty—though there are useful applications in 2D in-plane motion;
3) human in the loop control—surgeons prefer systems that they can control in real time and are typically better than automatically guided robotic systems; and 4) minimizing radius of curvature—for better control and wider variety of paths/obstacle voidance.

The first and last issues are a result of the stiffness trade-off. The needle must be strong enough to penetrate the tissue and maintain good control of where it goes, but must be flexible enough to have a tight turning radius (item 4). In addition, a higher stiffness will distort the tissue as the needle passes through the tissue which requires a better needle/tissue model. Thus, there is a desire for a needle that will be very stiff when it needs to penetrate and very flexible when it needs to bend.

Steerable needles known in the art are typically limited to simple, large curves. There is a need for a steerable needle that is capable of complex curves, as well as a small turning radius to enable small curvatures.

Besides having a small turning radius to enable more versatility in maneuvering the steerable needle, better controllability of the positioning of the needle is also desirable. One of the main factors that adds uncertainty in the control of positioning of a needle comes from the reaction forces from the tissue on the needle as it moves through the tissue.

Reaction forces are what guide the needle as it moves through turns. However, forces from the needle itself will also distort the tissue by varying amounts. As tissue stiffness varies this distortion is also difficult to predict and model.

An object of the present invention is to provide a steerable needle device that addresses one or more of the disadvantages of existing needles. The steerable needle of the present invention may provide the ability to create and follow a path through soft tissue that has multiple sharp curves. That is, as the needle is pushed into the tissue, an operator may steer the needle around obstacles and sensitive areas with high maneuverability. The present invention may also provide the ability for the needle body to be stiff when straight and flexible when bent, such that the path of the needle may be controlled more precisely without significantly distorting the tissue. The proposed invention may also provide an improvement in the minimum turning radius.

SUMMARY

In meeting the long-felt needs described above, the present disclosure first provides steerable needles, comprising: a shaft comprising a beam capable of being controllably buckled; a steering head positioned at a distal end of the shaft; a transmission for controlling the orientation of the steering head; and a base positioned at a proximal end of the shaft.

Further provided are steerable needles, comprising: a first tape spring comprising a first steering head adapted for insertion into a living subject, the first steering head located at a distal end of the first tape spring, the first tape spring having a mechanical bias in a first direction; a second tape spring comprising a second steering head adapted for insertion into a living subject, the second steering head located at a distal end of the second tape spring, the second tape spring having a mechanical bias in a second direction opposite the first direction, the first and second tape springs being engaged with one another such that the mechanical bias of the first tape spring counters the mechanical bias of the second tape spring, the first and second tape springs being further engaged with one another such that upon advancement of the first steering head beyond the second steering head, the first steering head translates in the direction of the mechanical bias of the first tape spring, and the first and second tape springs being further engaged with one another such that upon advancement of the second steering head beyond the first steering head, the second steering head translates in the direction of the mechanical bias of the second tape spring.

Further provided are steerable needles, comprising: a first tape spring comprising a first steering head adapted for insertion into a living subject, the first steering head located at a distal end of the first tape spring, the first tape spring being disposed within a shaft (which may comprise a beam), the shaft capable of being controllably buckled, and a transmission in mechanical communication with the steering head, the transmission being configured to change an orientation of the steering head, the change of the orientation of the steering head giving rise to a bend in the shaft as the steerable needle is advanced into a subject.

Also provided are methods, the methods comprising inserting a steerable needle according to the present disclosure into a subject.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various aspects discussed in the present document. In the drawings:

FIGS. 8A to 8E provide a sequence of motions of a steerable needle according to the present disclosure, making multiple bends;

FIGS. 9A to 9E show the steerable needle of FIGS. 8A to 8E from the opposite angle;

DETAILED DESCRIPTION OF ILLUSTRATIVE EMBODIMENTS

Figure 1:
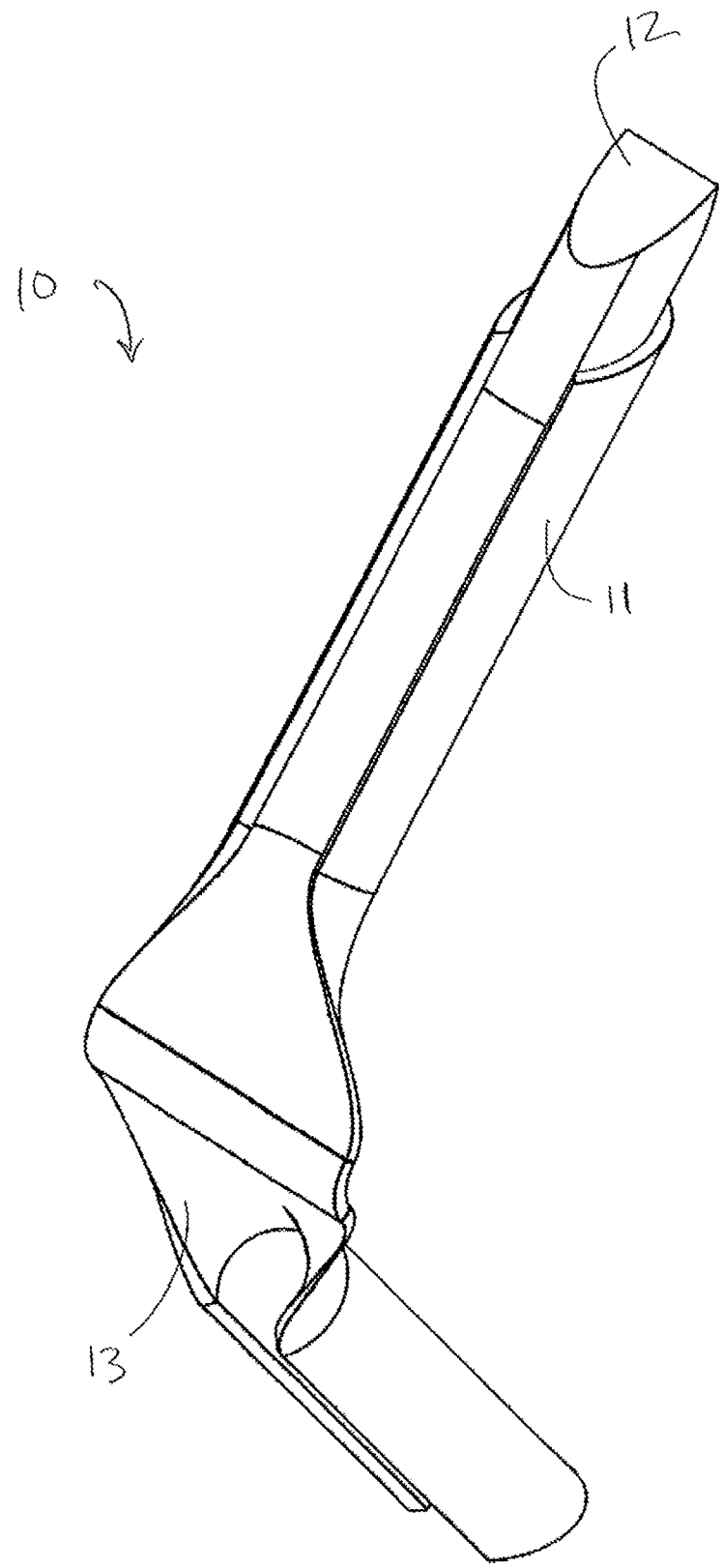
FIG. 1 shows a schematic representation of a steerable needle according to an embodiment of the present invention.

The present disclosure may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable, and it should be understood that steps may be performed in any order.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range. In addition, the term "comprising" should be understood as having its standard, open-ended meaning, but also as encompassing "consisting" as well. For example, a device that comprises Part A and Part B may include parts in addition to Part A and Part B, but may also be formed only from Part A and Part B.

One aspect of the present invention relates to a steerable needle comprising a shaft, a steering head positioned at a distal end of the shaft, a transmission for controlling the orientation of the steering head, and a base positioned at a proximal end of the shaft.

The shaft of the steerable needle may comprise a beam that can be controllably buckled. As used herein, the term "controllably buckled" means that a bend can be induced in the beam at a desired location, e.g., at the distal end of the shaft, by applying a moment of force on the shaft.

The beam may have any geometry capable of penetrating tissue and being controllably buckled. For example, the beam may comprise a straight beam, an angled beam, and shaped beams such as L-beams, C-beams, etc. The beam may have a uniform cross-section or have a non-uniform cross-section, such as, for example, a tapered cross-section.

According to at least one embodiment, the shaft of the needle comprises a curved spring formed from a flattened tube or a straight beam, also referred to as a tape spring. (One non-limiting example of a tape spring is a standard metallic household tape measure.) The (at least) partial tube created by the tape spring maintains axial stiffness when straight, but can be controllably buckled along the shaft of the needle, such as at the distal end, or head, of the needle. Nominally the beam is straight and acts as a straight needle would. However, when a curved path is desired, a bend is induced at the distal end of the needle.

The steerable needles according to embodiments of the present invention may be capable of executing multiple or complex curves. In at least one embodiment, the steerable needle is capable of making multiple turns in three-dimensions.

In accordance with an embodiment of the present invention, the steerable needle may have a turning radius of less than 50 mm, such as, for example, less than 35 mm, less than 25 mm, less than 20 mm, less than 15 mm, less than 10 mm, less than 5 mm, less than 4 mm, less than 3 mm, less than 2 mm, or even less than 1 mm. The disclosed steerable needles may have a turning radius of, e.g., from about 1 to about 50 mm, from about 2 to about 45 mm, from about 3 to about 40 mm, from about 4 to about mm, or even from about 5 to about 20, 25, or even about 30 mm. Turning radii of from about 1 to about 15 mm are considered suitable, e.g., from about 1 to about 15 mm, from about 2 to about 15 mm, from about 3 to about 15 mm, from about 4 to about mm, or even from about 5 to about 15 mm.

In prior art steerable needles, it may be necessary to carefully model the tissue and curvature of the needle to traverse tissues of varying stiffness, which required precise knowledge of the tissues involved. The stiffness of the tissues, however, can and usually does change over time. Therefore, the stiffness of the tissue often changes between the time of initial analysis and the operation.

Propagation of bends in the steerable needle according to the present disclosure may add negligible strain energy, so there may be little stress put on the tissue to maintain the shape in the tissue (little tissue distortion) in contrast to the bevel-tip needles. Because of this, steerable needles according to embodiments of the present disclosure may have more precise control through tissues with varying stiffness (as one would find in actual surgeries) without strongly affecting the path of the needle. Therefore, the shape of the path of the steerable needles according to embodiments of the present disclosure may be less prone to errors, allowing them to be more accurate and precise in placement.

Once a turn is initiated with a bend in the beam, that that bend traverses along the beam as the needle progresses into the tissue. Once a bend is induced in the beam, it takes nearly zero energy to propagate that bend down the beam. The strain energy required to bend a straight portion an incremental distance down the beam is recovered in the strain energy of the curved part that is straightening.

Nominally, bends introduced in a beam such as a tape spring can only occur along one plane due to the nature of the beam. For example, tape springs can bend inward and outward, but not side to side. That is the needle's curving path can only reach points on a 2D plane. According to at least one embodiment, full 3D arbitrary positioning can be obtained by rotating this 2D plane by adding a mechanism to introduce a screw-like twist in the head. In this manner the bending 2D plane can controllably rotate along the longitudinal axis of the needle allowing arbitrary 3D positioning. The twist rate will require some distance to rotate and this twist may create reaction forces in the tissue to maintain the twist shape.

The shaft of the steerable needle may provide the primary mechanism by which the needle can be stiff in straight portions and flexible in bent portions to curve or turn within tissue.

The steering head of the steerable needle according to embodiments of the present disclosure is positioned at the distal end of the needle shaft and leads the path of the needle and induces bends in the path, thereby controlling the direction of the needle as commanded by a user, such as, for example a surgeon. The steering head may be an integral part of the shaft of the needle, or alternatively, the steering head may be a separate component, e.g., a solid tip placed at the distal end of the needle shaft. According to at least one embodiment, the steering head comprises the distal end portion of the needle shaft, which may be contoured or shaped to penetrate and guide the steerable needle through the tissue.

A user may use the steering head to perform a surgical procedure (e.g., an excision or trimming procedure). Alternatively, a user may feed one or more other instruments (e.g., a scope, a light, a probe, a suction tube, a cutting device, a biter, a clamp, a suturing/stitching device, an ablation modality, and the like) through the steerable needle to a location of interest. A user may insert a given instrument, use the instrument, withdraw the instrument, and then insert an alternative instrument.

The disclosed steerable needles may also be used to form a bent, curved, or otherwise tortuous pathway within a patient, e.g., between an organ and the patient's skin, between two tissues, and the like. Once the tortuous pathway is formed, a user may remove the steerable needle and place a tube and/or stent to maintain the tortuous pathway for future use. Suitable tubes and stents are known to those of ordinary skill in the art, and a user may place a single tube or stent or multiple tubes and/or stents into the formed pathway.

The base is at the proximal portion of the needle outside the body at the interface with the user. The base may comprise a controller for controlling the steering head.

The transmission in the steerable needle transmits forces and torques from the base to the steering head. The transmission may be a component separate from the shaft of the needle, or the shaft of the needle itself may function as the transmission. For example, a needle shaft comprised of two beams joined at the distal end of the shaft may transmit forces and torques by manipulating the beams independently, e.g., applying more force to one of the beams may induce a bend at the steerable head.

FIG. 1 shows a steerable needle 10 according to an embodiment of the present disclosure. Steerable needle 10 comprises a beam in the form of a tape spring 11 and a steering head 12. In FIG. 1, steering head 12 comprises a symmetric stylet. Steering head 12 comprises a beveled surface for piercing the tissue. The steerable needle 10 has a transmission 13 comprised of an inner tape spring, which is concentric to the tape spring 11 that makes up the shaft of the steerable needle.

It should be understood that a steering head may be a beveled tip. A steering head may also be conical or multi-faceted in configuration. A steering head may be hollow (e.g., defining a lumen) so as to allow for delivery of an agent, a device, a sensor, or other payload to a subject or patient. A steering head may be smooth, but may also comprise teeth, threads, cutting edges, or other surface features configured to cut and/or penetrate tissue. A steering head may also be formed such that it may be expanded and/or contracted. For example, a steering head may be formed of two or more "petals" which may be flared out—or folded in—during deployment. In this way, such a steering head may be deployed in a reduced-size configuration so as to ease insertion into the subject, and then the head's petals may be flared out so as to increase the cross-sectional area of the pathway that the head forms in the subject's tissue during deployment. Petal-type steering heads are not the only configuration for an expandable steering head; expandable steering heads may be expandable in a telescoping- or iris-style fashion.

A steering head may be tapered, but may also be flared in cross section, as there is no requirement that the exterior cross-sectional dimensions of the steering head (e.g., diameter) be smaller or equal to the outermost exterior cross-sectional dimensions of the steerable needle. As one example, a steering head may have a cross-sectional diameter that is greater than the exterior cross-sectional diameter of the steerable needle. In this way, the steering head may act to clear a path through tissue that is wider than the steerable needle.

The steering head may also be hollow so as to allow for withdrawal of material (e.g., blood, spinal fluid, tissue, sensor, and the like) from a patient. The lumen of the steering head may be in fluid communication with a conduit used to deliver or withdraw material from or through the steering head. In some embodiments, the conduit may be a flexible tube that is engaged with the steerable needle, e.g., a flexible tube disposed along an inner tape spring of the steerable needle.

In some embodiments, the lumen of the steering head may be in fluid communication with a lumen of the steerable needle. As one example, a steerable needle may comprise an inner tape spring that is a flattened tube (i.e., ovoid) in cross-section. The steerable needle may include a steering head that has a lumen that is in turn in fluid communication with the lumen of the flattened tube inner tape spring.

In at least one embodiment, the steering head may comprise a symmetric stylet, as shown in FIG. 1. A symmetric stylet can be used for two-dimensional planar motions, such as, for example, when inward and outward turns are required.

Figure 2A:
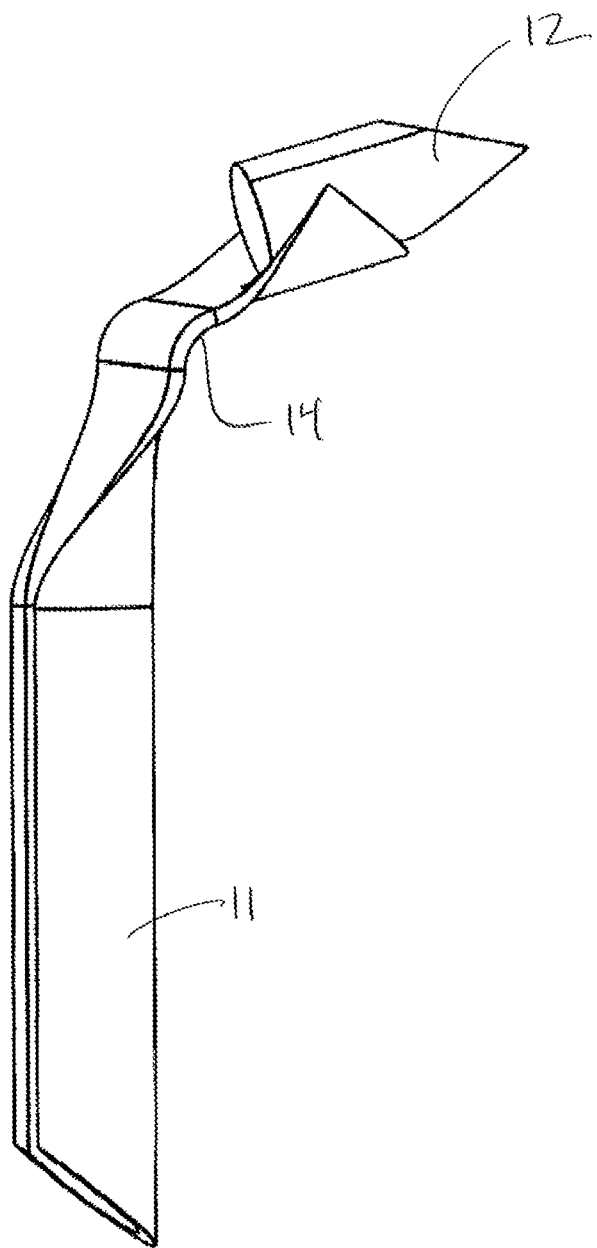
FIGS. 2A and 2B show the initiation and translation of an inward bend down the shaft of a steerable needle according to an embodiment of the present invention.
Figure 2B:
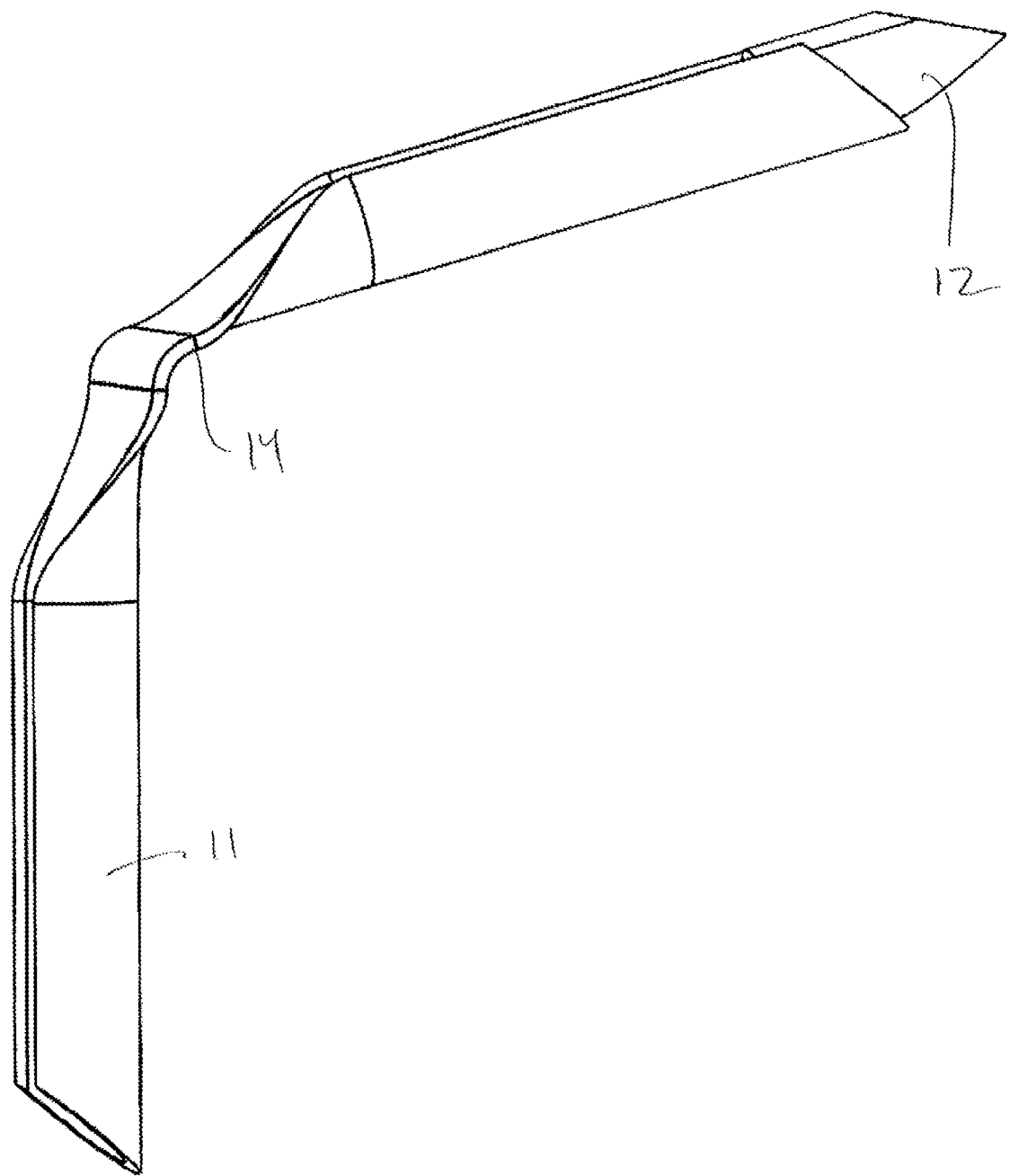

FIGS. 2A and 2B shows how bends are initiated and propagated in a steerable needle according to an embodiment of the present disclosure. In FIG. 2A, a bend 14 is initiated in the tape spring 11 at the distal end of the steerable needle at the steering head 12. The bend 14 is initiated by the transmission (not shown) to buckle the tape spring 11 inward. As the steerable needle is pushed further into the tissue, the bend 14 propagates down the length of the tape spring 11.

When inserted into tissue, the steering head in the nominal or neutral position will lead to straight paths. Engaging the transmission, e.g., pulling on a control linkage, in one direction will cause a moment at the steering head, bending the tape spring locally, as shown in FIG. 2A. As insertion of the needle continues, the currently bent portion will straighten leaving that bend in the path (FIG. 2B). The work required to induce this bend is input from a user (e.g. surgeon) at the base (not shown) of the steering needle outside the tissue and transmitted to the head. Advantageously, the supplied forces to apply this moment can be arbitrarily large in comparison to prior art steerable needles based on bevel tip methods that rely on tissue interaction forces for turns.

Figure 3A:
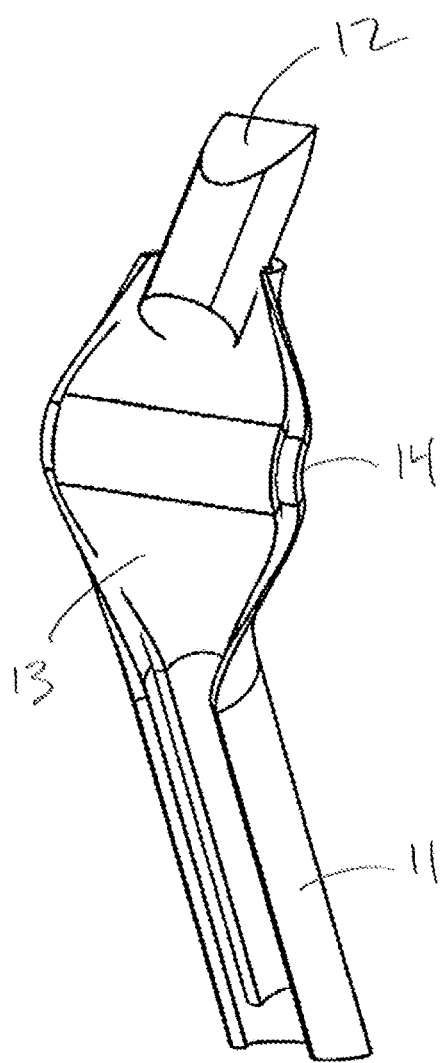
FIGS. 3A and 3B show the initiation and translation of an outward bend down the shaft of a steerable needle according to an embodiment of the present invention.
Figure 3B:
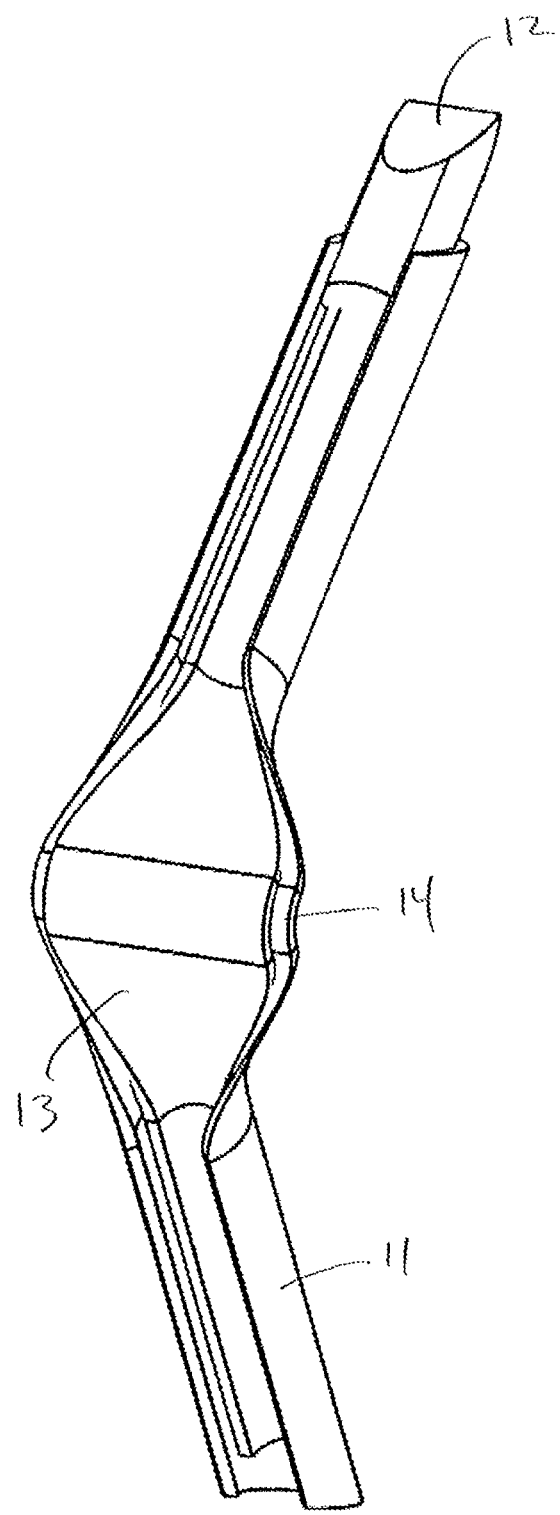

Similarly, as shown in FIGS. 3A and 3B, engaging the transmission 13 in the opposite direction, e.g., pushing a stiff control linkage, can cause a moment in the opposite sense to induce a bend 14 in the tape spring 11 in the other direction. The bend 14 is initiated in the tape spring 11 near the steering head 12, as shown in FIG. 3A. In FIG. 3B, further insertion of the steerable needle 10 causes translation of the bend 14 down the length of the tape spring 11.

In FIGS. 3A and 3B, the transmission 13 comprises a tape spring concentric within the tape spring 11 of the needle shaft. The tape spring of the transmission 13 can be fixed at the distal end of the steerable needle 10 to exert the necessary force on the tape spring 11 to induce bends in the tape spring 11 and change the direction of the steerable needle 10. Pulling on the tape spring of the transmission 13 will induce an inward bend, whereas pushing on the tape spring of the transmission 13 will induce an outward bend.

As used herein, the term "inward" refers to the interior, or concave portion, of a beam. For a tape spring, inward applies to the concave or semi-circular region of the tape spring created by the curvature of the tape spring around the longitudinal axis. Similarly, the term "outward" refers to the exterior of the beam. For a straight beam having identical faces, the terms "inward" and "outward" are equivalent and can be arbitrarily defined for the sake of convenience.

According to embodiments of the present disclosure, the transmission may comprise a linkage such as, e.g., a control wire, a flexible tube, a rod, or a tape spring, as shown, for example, in FIGS. 3A and 3B. In at least one embodiment, the transmission comprises a tape spring. It should be understood that in any embodiment of the disclosed steerable needles, a transmission may effect movement of a steering head in a plane. A transmission may also, as described elsewhere herein, effect rotational motion of a steering head, e.g., via a twisting moment. A transmission may comprise, e.g., four linkages (e.g., wires) arranged—in the cross-section of the steering head—at 12 o'clock, 3 o'clock, 6 o'clock, and 9 o'clock. In this way, a user may actuate one, two three, or all four of the linkages so as to effect movement of the steering head in virtually any direction.

Figure 11:
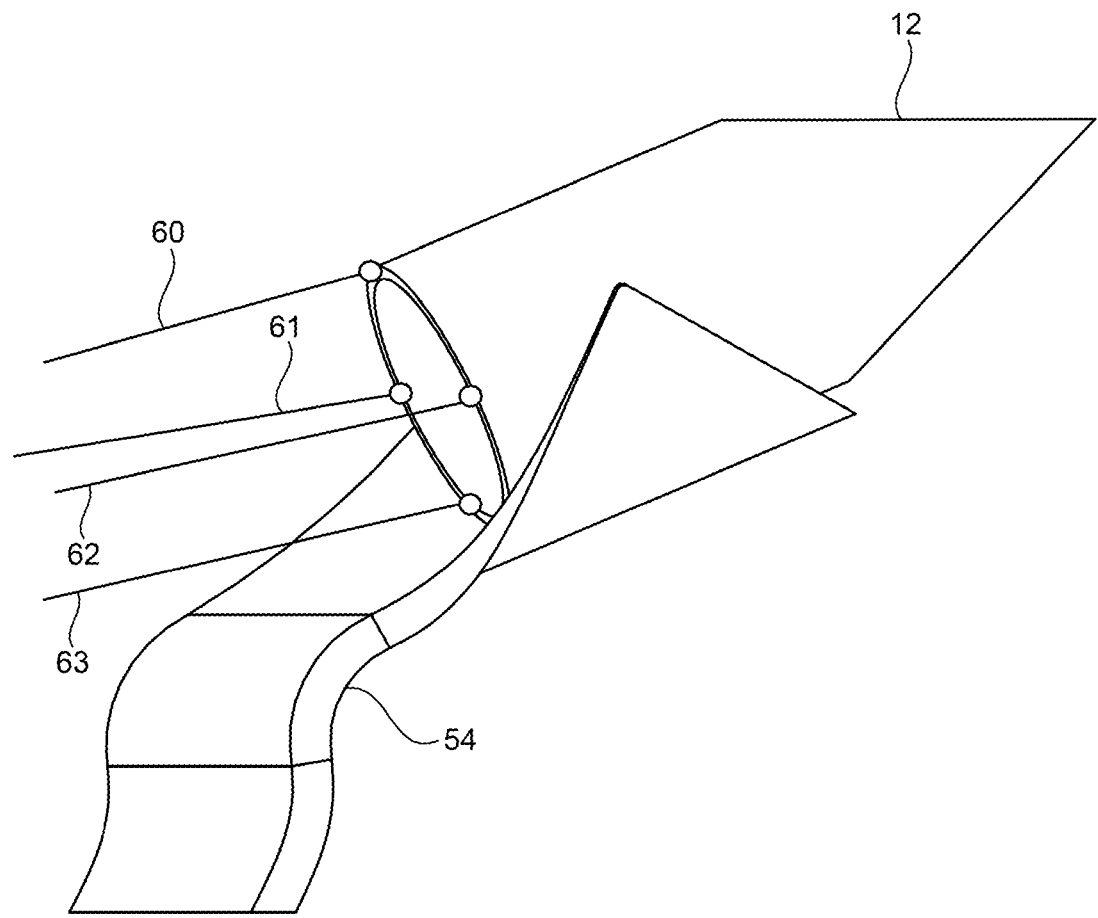
FIG. 11 shows an embodiment of a steerable needle according to the present disclosure.

This is shown in FIG. 11, which shows a steerable needle according to the present disclosure, the needle including bend 54. Steering head 12 has four linkages (60, 61, 62, and 63) attached at various points around the steering head. By actuating one or more of the linkages, a user may effect movement of the steering head in virtually any direction. (It should be understood that the linkages in FIG. 11 are shown extending outwardly from steering head 12 for clarity; the linkages may of course be flexible and be disposed along or within the steerable needle.

Alternatively, the transmission may induce bends in the steerable needle through the application of heat, electricity, magnetic fields, or other external forces. For example, the transmission may comprise a shape memory alloy, such as nitinol, which can alter its shape, i.e., apply a force, upon the application of heat. Similarly, the transmission may comprise an electrically activated material to exert a bending force, such as, for example, an electro-active polymer. In at least one embodiment, the transmission may be controlled through magnetic fields. For example, the steerable head may comprise a material that can be manipulated by a magnetic field that may be externally applied to induce a bend in the shaft of the needle. The externally applied magnetic field may be positioned, for example, outside of the subject, but may also be from within or on the steerable needle or another device. The transmission may be separate from the tape spring forming the shaft of the steerable needle, or be incorporated into the shaft itself. A bending or twisting force may be effected by, e.g., a magnetic force (as mentioned), by heat (e.g., via use of a bimetallic joint that may bend in a particular direction in response to heat), and the like.

In at least one embodiment, the transmission is flexible so that it can induce a bend in the steerable needle, yet is stiff enough that it can be pushed to bend the shaft of the flexible needle outward. When a stiff transmission is in a neutral position, the steerable needle will follow a straight path. When the stiff transmission is pushed (i.e., compression force applied), an outward bend in the tape spring of the needle shaft will be induced, and when the stiff transmission is pulled (i.e., tension force applied), an inward bend in the tape spring of the needle shaft will be induced.

If a stiff transmission is not viable in the desired application for pushing, embodiments of the present disclosure may use a beam having a bias in the needle shaft so that the nominal rest-position of the beam is bent away (i.e., outward) from the transmission. By including a bias in the beam of the needle shaft, only pulling or tension in the transmission is required to direct the steerable needle straight, inward, or outward. When the transmission is not pulled, the steerable needle will be directed outward. Increasing the amount of tension on the pulled transmission will cause the steerable needle to go straight, and even more tension on the pulled transmission will induce an inwardly direct bend in the steerable needle. Thus, a steerable needle having a bias in the beam will require only different magnitudes of pulling to obtain straight paths or turning in either direction.

In other embodiments, the transmission may not rely on creating axial tension/compression (i.e., pulling/pushing) and instead may transmit force/torque by twisting. In at least one embodiment, a shaft (e.g., a threaded shaft) or other interface may be incorporated at the steering head allowing the transmission to twist axially to rotate the threaded shaft (without inducing twist in the needle body). The threaded shaft translation then induces similar bending at the steering head.

Figure 4:
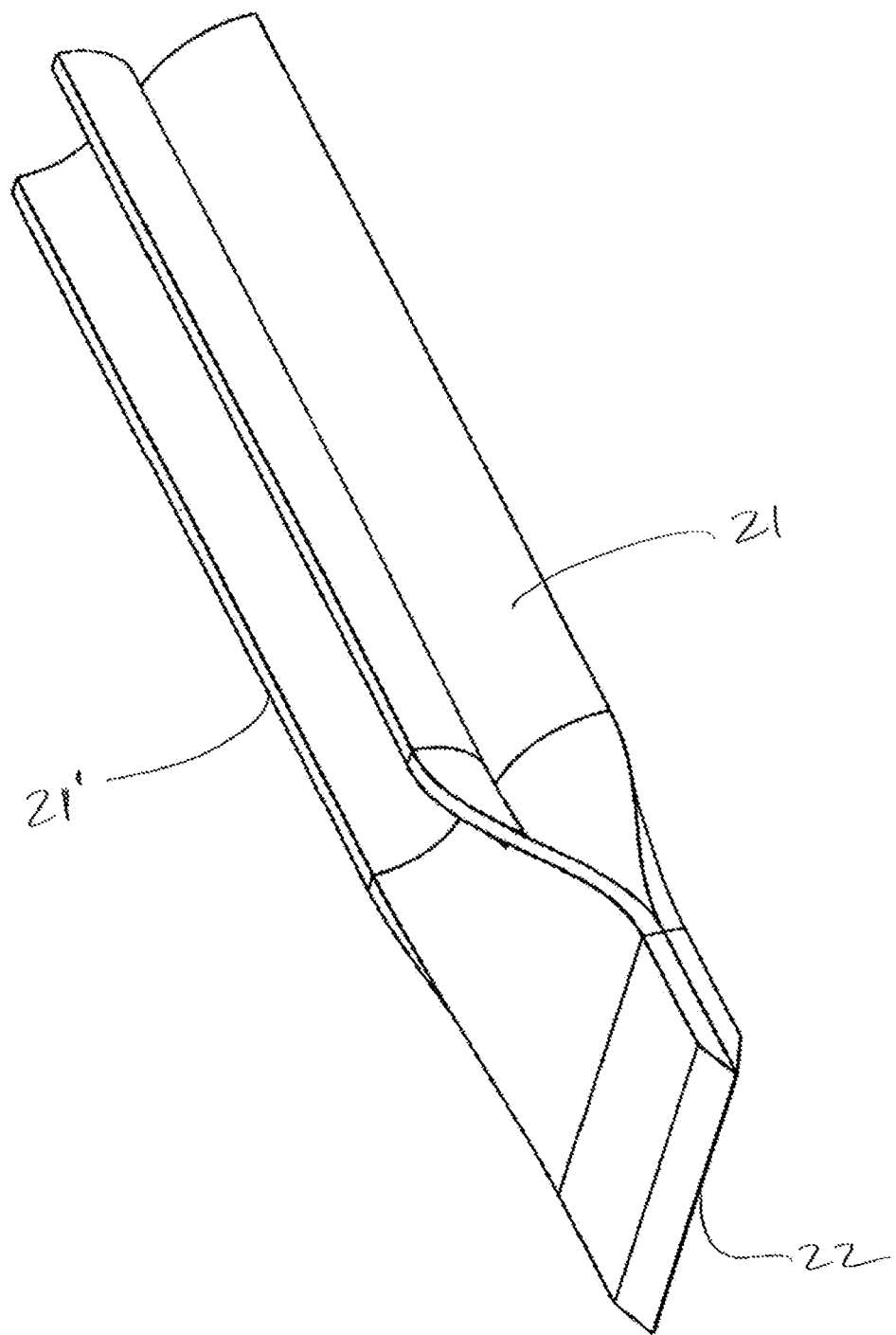
FIG. 4 shows a steerable needle comprising two tape springs according to an embodiment of the present invention.

FIG. 4 shows an embodiment in which the beam of the needle shaft itself serves as the transmission. As shown in FIG. 4, the steerable needle 20 comprises two similar tape spring elements 21, 21' lined up back to back, i.e., the convex side of the tape springs are adjacent, and the two tape springs 21, 21' are attached at the steering head 22. In other words, the two tape springs 21, 21' serve as both the shaft of the steerable needle 20 and as the transmission. The steering head 22 consists of the two ends flattened and joined at a sharpened tip. Steering occurs by pushing or pulling differentially on the two tape springs 21, 21'.

Figure 5:
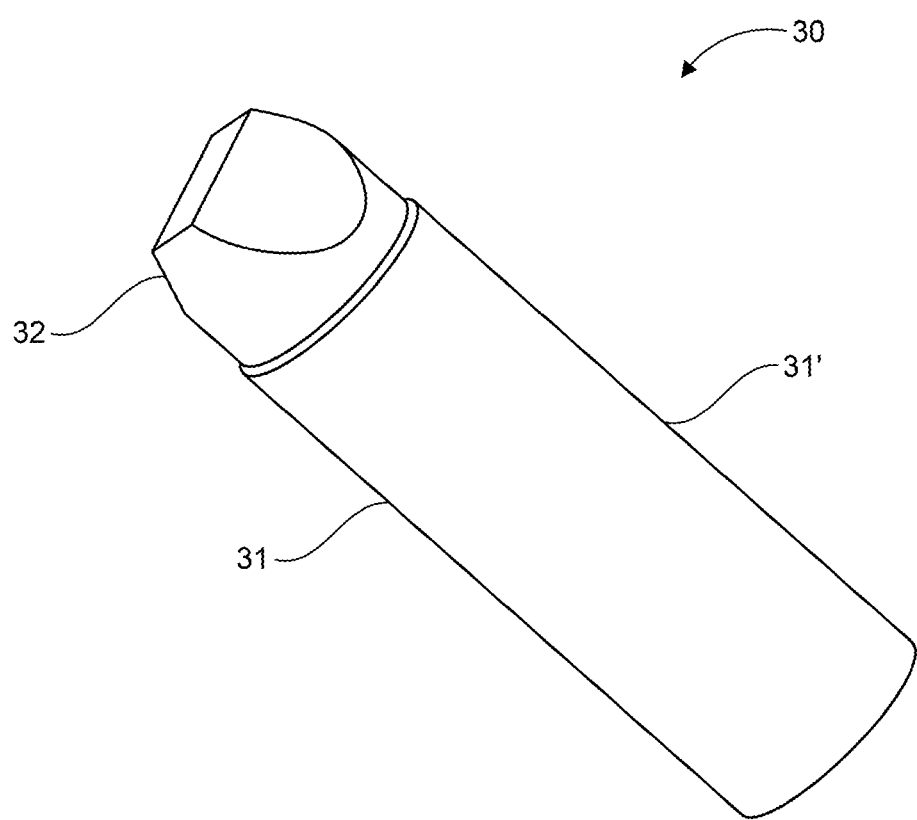
FIG. 5 shows a steerable needle comprising two tape springs according to an embodiment of the present invention.

FIG. 5 shows another embodiment using a tape spring for a transmission. As shown in FIG. 5, steerable needle 30 comprises two similar tape spring elements 31, 31' lined up such that the concave sides of the tape springs are aligned, creating a closed tube. The two tape springs 31, 31' may be attached at (or even attached only at) steering head 32, allowing the steerable needle 30 to be directed by independently pushing or pulling on the tape springs 31, 31'. In some embodiments, one of the tape springs may be considered a beam, and the other tape spring may be considered a transmission. It should be understood that a beam may also be used to effect a change in orientation of a steering head.

When the needle shaft is an open beam, i.e., not a closed tube, pulling or pushing on the transmission can cause the transmission to separate from the needle shaft (e.g. a control wire or other linkage at a bend may cut the corner), which may result in loss of control at the steering head and cause damage to the tissue. There are several ways to mitigate this and to keep the transmission contained within the desired path of the steerable needle. According to at least one embodiment, the transmission is contained within the confines of the needle shaft.

In at least one embodiment, the beam of the steerable needle comprises a flattened tube. The use of a flattened tube allows a transmission, e.g., control wires, to be contained inside the tube. The flattened tube may be relatively flat or planar, e.g., approximating the form of a straight beam, or the flattened tube may have an angle or curvature, e.g., approximating the form of a C-beam or L-beam.

In accordance with at least one embodiment, the beam of the steerable needle has at least one feature within the structure of the beam to constrain the transmission. The feature may contain the transmission and keep the transmission within the desired path of the steerable needle.

Figure 6A:
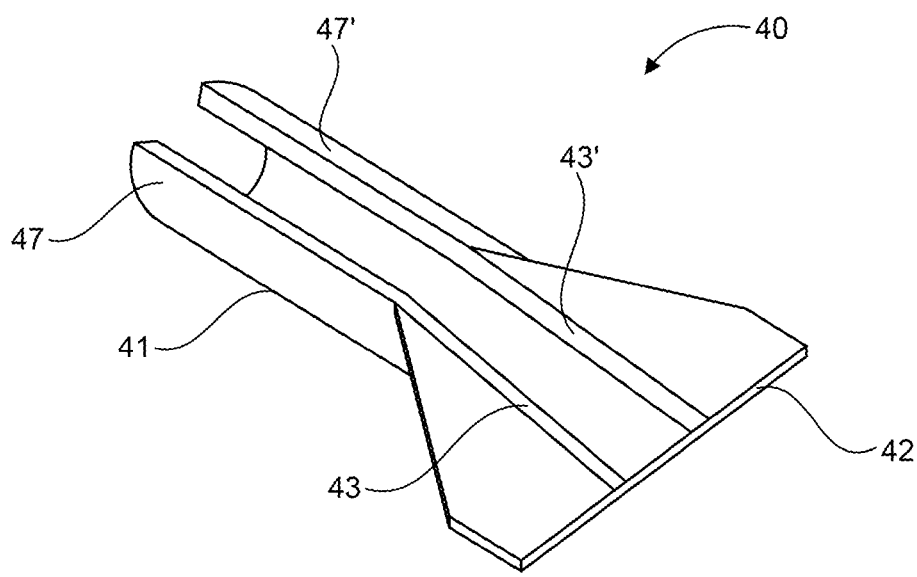
FIGS. 6A and 6B show the use of two control linkages (e.g., wires) providing a screw-like twist in a steerable needle according to an embodiment of the present invention.

In at least one embodiment, the feature comprises a channel. The channel may be positioned at an edge of the beam. In at least one further embodiment, the beam comprises a channel positioned at each side of the beam. FIG. 6A provides an example of a steerable needle 40 wherein the shaft of the need comprises a tape spring 41 having a channel 47, 4'T on each side of the tape spring 41. Two control linkages 43, 43' reside in respective channels 47, 47' to control steering head 42.

Figure 6B:
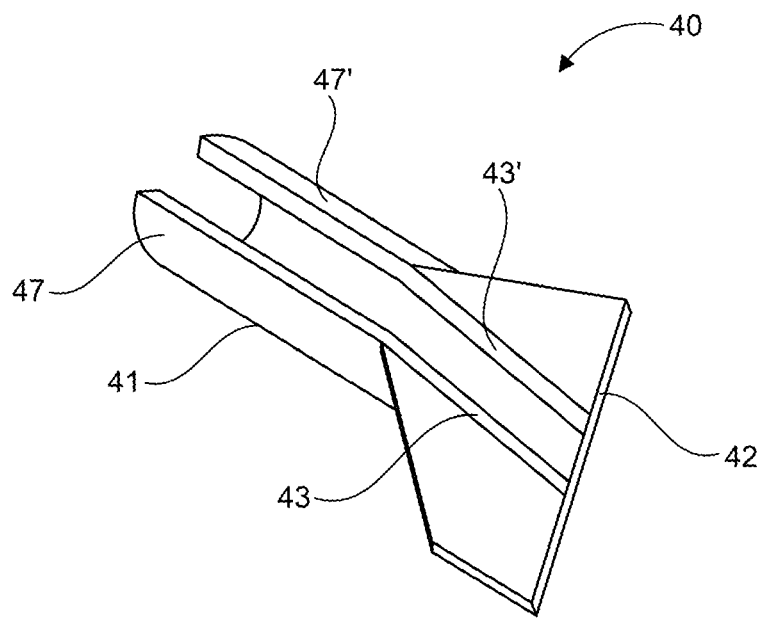

As shown in FIG. 6B, the use of two control linkages 43, 43' allows for the induction of a screw-like twist in the steering head 42. By independently pulling on one of the control linkages 43, 43' the steering head 42 rotates with respect to the tape spring 41. The twisting motion of the steerable needle 40 shown in FIG. 6B differs from the motion of the bevel-tip steerable needles of the prior art.

Figure 7:
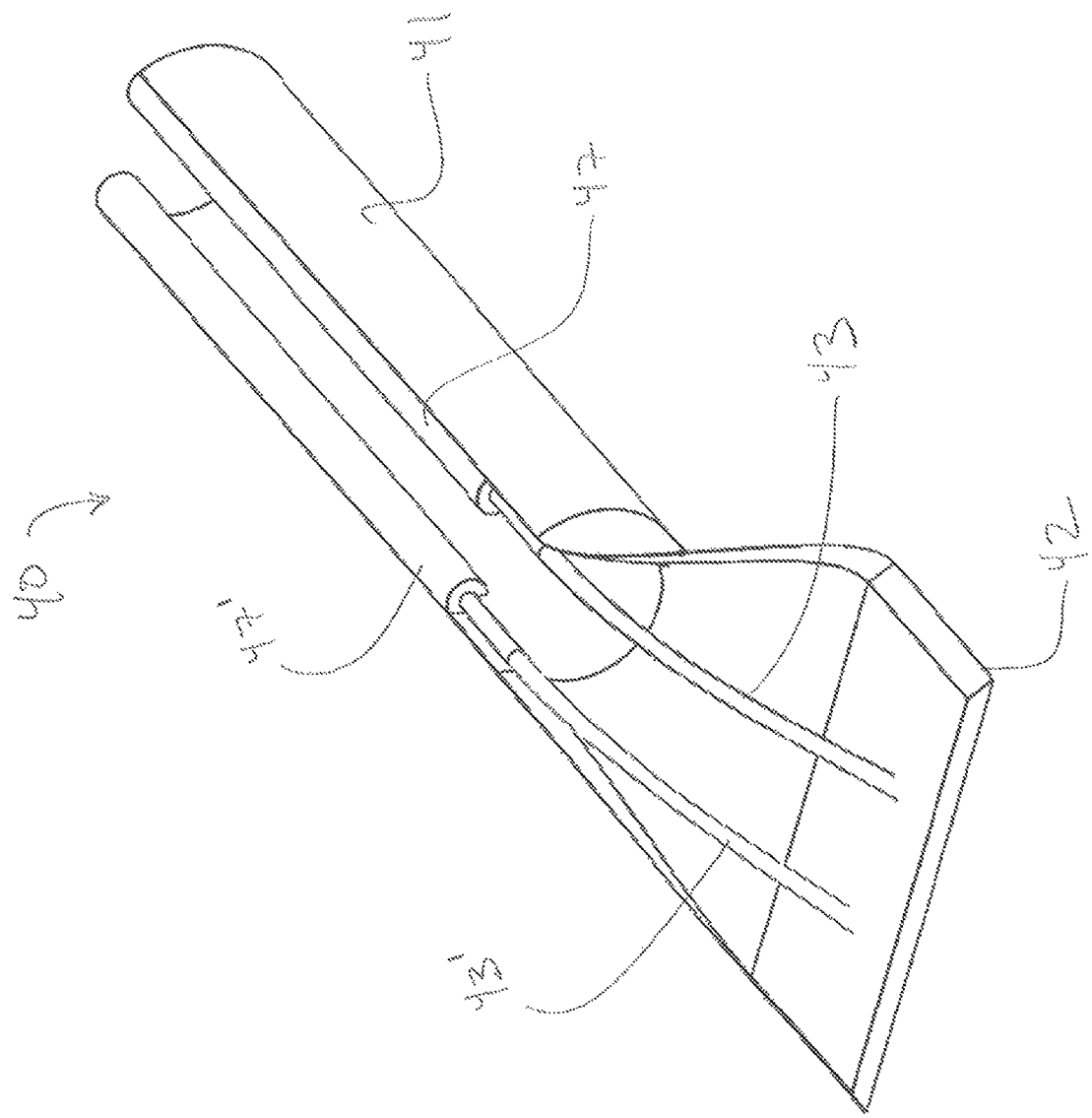
FIG. 7 provides additional detail of an embodiment that features control linkages that permit a screw-like twist in a steerable needle according to the present disclosure.
Figure 10A:
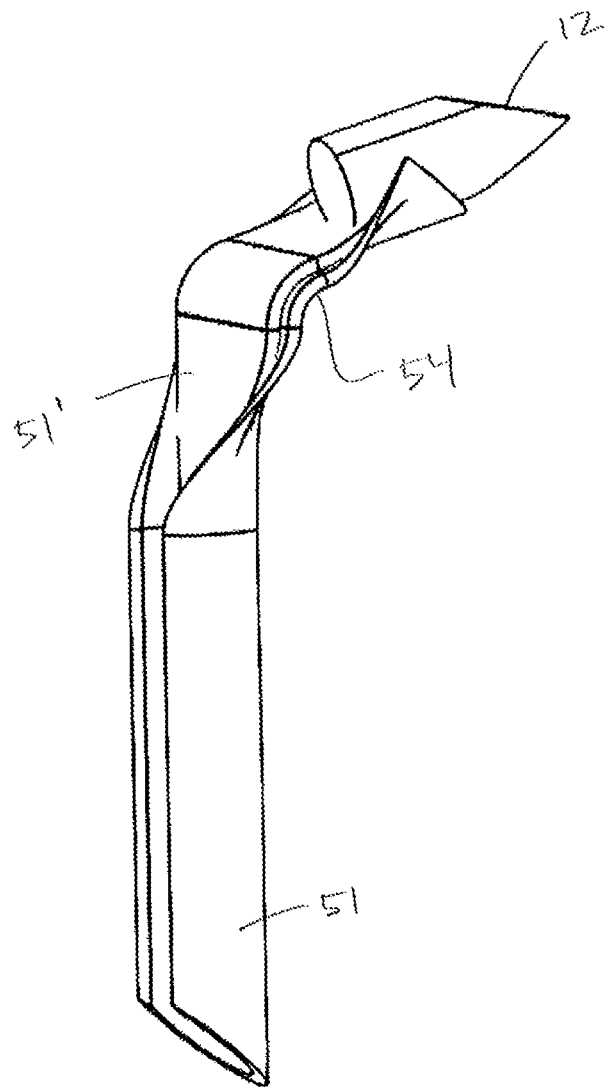
FIG. 10A shows a steerable needle according to the present disclosure making a bend.
Figure 10B:
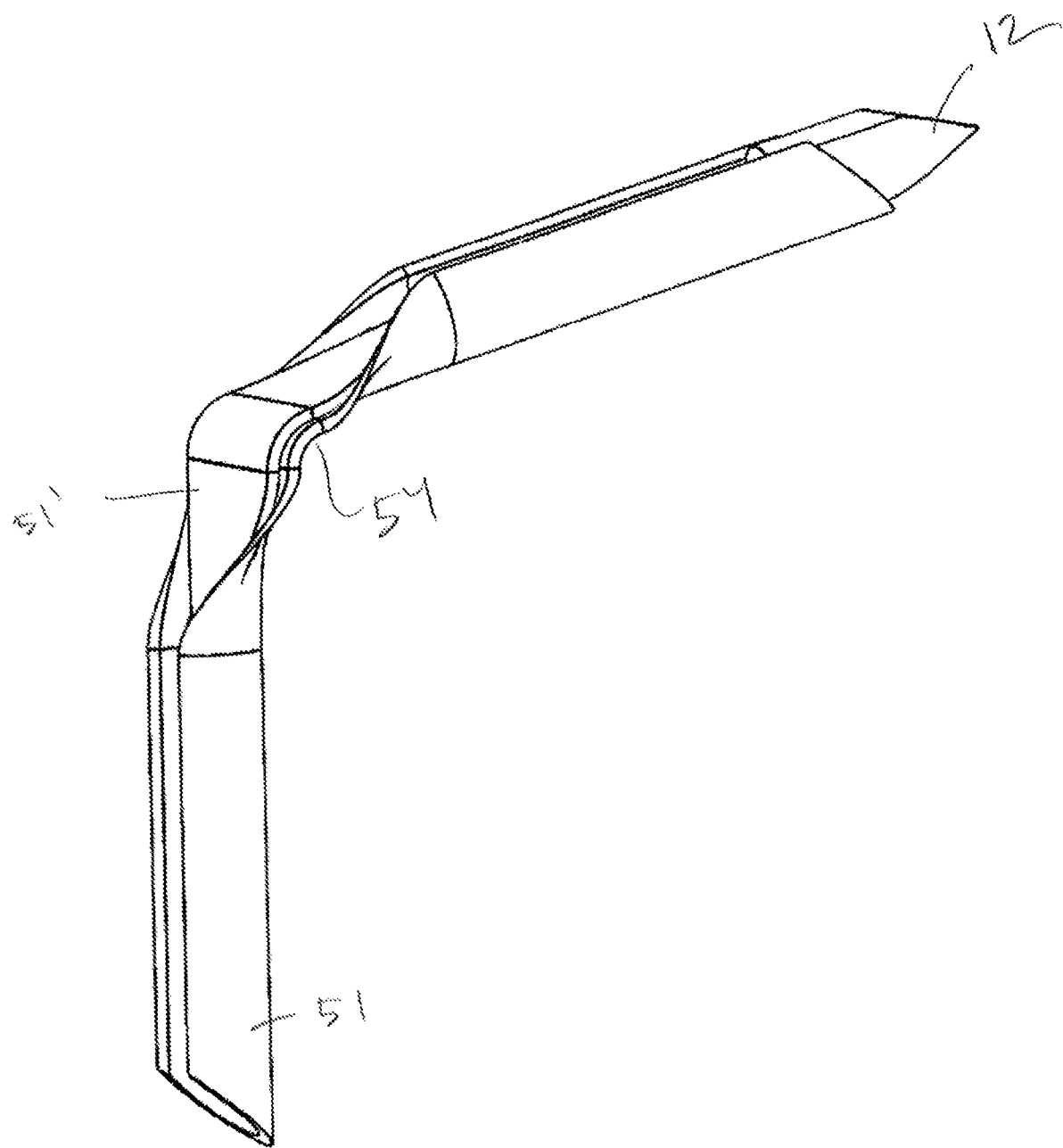
FIG. 10B shows the steerable needle of FIG. 10A in a further extended configuration.

FIG. 7 provides a magnified view of an exemplary steerable needle 40 according to the present disclosure. As shown, steerable needle 40 may have a shaft that in turn comprises a tape spring 41 having a channel 47, 47' on each side of the tape spring 41. Two control wires 43, 43' reside in respective channels 47, 47' to control steering head 42. As described in FIG. 6B, the use of two control wires 43, 43' allows for the induction of a screw-like twist in the steering head 42. By independently pulling on one of the control wires 43, 43' the steering head 42 rotates with respect to the tape spring 41. The twisting motion of the steerable needle 40 shown in FIG. 6B differs from the motion of the bevel-tip steerable needles of the prior art.

The prior art devices are twisted at the base and the needles are torsionally stiff. In the steerable needle according to the present embodiments, the twist is induced at the steerable head and the shaft of the needle does not need to be torsionally stiff. The torsional stiffness affects how far the needle must travel through the tissue for the bending plane to twist a given amount. By using a beam that is not torsionally stiff, the needle does not need to travel far through the tissue for the bending plane to twist. Thus, the steerable needles according to embodiments of the present disclosure may have a significantly improved turning radius.

According to at least one embodiment, the shaft of the steerable needle comprises two beams, such as, for example, tape springs. With two beams, one beam can be used to apply some of the reaction force components thus reducing the forces applied to the surrounding tissue reducing distortion and tissue damage.

Local distortion of the tissue is larger for a given force from the needle if the force is applied to a smaller area (e.g. the pressure on the tissue is larger). When a needle begins to make a sharp turn, the area on the tissue from which reaction forces are required to guide the needle to turn is at its smallest. Not only will the tissue distort a larger amount, but the needle may not turn, because the tissue may tear, or the needle head may completely fold over so the needle continues in a straight line.

FIGS. 8A to 8E (and 9A to 9E) depict a sequence of bends undergone by exemplary steerable needle 50, with viewpoints from either side of the sequence of turns. Steerable needle 50 may comprise two nested concentric tape springs 51, 51'; the tape springs 51, 51' are referred to as the outer tape spring and the inner tape spring, respectively. Each tape spring 51, 51' may have a small sharpened steering head 52, 52' (respectively).

In the illustrative embodiments shown in FIGS. 8A to 8E, outer tape spring 51 is inwardly biased, and inner tape spring 51' is outwardly biased. Thus, the bias in tape springs 51, 51' serves as the transmission. Therefore, when the distal end of outer tape spring 51 advances beyond the distal end of inner tape spring 51', the inward bias of outer tape spring 51 induces an inward bend in the steerable needle 50. When inner tape spring 51' is advanced, inner tape spring 51' will follow the path defined by outer tape spring 51.

Similarly, when the distal end of inner tape spring 51' is advanced beyond the distal end of outer tape spring 51, the outer bias of inner tape spring 51' will induce an outward bend in the steerable needle 50. Advancing outer tape spring 51 will cause outer tape spring 51 to follow the path defined by inner tape spring 51'.

The inward and outward biases of outer tape spring 51 and inner tape spring 51', respectively, can be designed such that the biases counter each other when the tape springs 51, 51' are advanced together, i.e., a straight path is followed when the distal ends of the tape springs 51, 51' are advanced together.

FIGS. 8A to 8E show a sequence of motion in which multiple bends are induced and translated down the length of a steerable needle 50 from the outer surface of the steerable needle 50. FIGS. 9A to 9E show the same sequence of motion from the inner surface of the steerable needle 50.

As shown in FIGS. 8A and 9A, the steering heads 52 and 52' (respectively) of outer tape spring 51 and inner tape spring 51' are imposed on one another, the biases of the two tape springs counter one another such that when the tape springs 51 and 51' are advanced together, they move in a straight path. Thus, the steerable needle 50 is progressing in a straight line. The inner tape spring 51' and the outer tape spring 51 are aligned together.

As shown in FIGS. 8B and 9B, when steering head 52 is advanced beyond steering head 51', the bias in tape spring 51 results in the formation of a first bend 54. FIGS. 8B and 9B show the outer tape spring 51 moving forward a small amount with respect to the inner tape spring 51'. The steering head 52 of the outer tape spring 51 may be advanced and bends towards the inner beam by a controlled amount to induce a first bend 54 in the steerable needle 50.

Inner tape spring 51' (and steering head 52') may then be advanced such that steering heads 52 and 52' are even with one another, as shown in FIG. 8C and then in FIG. 8D, which figure shows that tape springs 51 and 51' advance together in a straight path through first bend 54 when steering heads 52 and 52' are superimposed on one another such that the biases of the respective tape springs 51 and 51' counteract one another. In FIGS. 8C and 9C, the inner tape spring 51' then moves forward with respect to the outer tape spring 51, following the bend 54 of the outer tape spring.

During the sequence shown in FIGS. 8C and 8D, the outer tape spring 51 provides the axial reaction force (the force along the long direction of the tape spring) to enable the inner tape spring 51' to make the turn without requiring that component of force from the tissue. This is the critical moment where the reaction forces from the tissue would have the smallest area and thus would distort or tear. The sequences shown indicates that the same condition can occur for bends in the other direction, but with the roles of each tape spring reversed It should be understood that in progressing from FIG. 8C to FIGS. 8D (and 9C to 9D), the two tape springs may be positioned together so as to progress in a straight line such that steering heads 52 and 52' are positioned even with one another.

As shown in FIGS. 8E (and 9E), the steering head 52' (not shown) may be advanced beyond steering head 52. As a result of this advancement, the bias in tape spring 51' results in tape spring 51' forming a second bend 56. Steering head 52 may then be advanced so as to advance tape spring 51 through second bend 56.

FIGS. 9A to 9E show the sequence of FIGS. 8A to 8E, from the opposite angle of steerable needle 50. As an alternative to using inward and outward biases in the tape springs, tape springs 51, 51' may use a transmission selected from any of the transmissions disclosed herein, including, but not limited to, e.g., one or more control linkages such as wires, flexible tubes, rods, tape springs, shape memory alloys, and electro-active polymers. In at least one embodiment, the transmission can be contained between the inner and outer tape springs.

According to at least one embodiment, the transmission for tape springs 51, 51' can comprise cables pulled in tension when attached to the steering heads 52, 52' to induce a bend in one direction. If the steering heads 52, 52' are biased or spring loaded to have a natural position at one of the bend extremes, the cable can be relaxed with no tension to have the steering head bend, pull with some tension to straighten, or pull with more tension to bend toward the opposite side. Alternatively, two cables can be used per tape spring to bend the steering head one way or the other if the natural position (i.e., no steering force applied) of the steering head is straight.

According to various embodiments of the present disclosure, attempts are made to minimize the reliance on forces on the tissue to guide the needle in order to improve controllability of the positioning. Minimizing stiffness in the buckled state (e.g. by having thin wall thickness and lower Young's modulus materials in the needle) is an example of one way in which the forces on the tissue from the needle can be minimized.

There are a variety of material properties that may influence the performance of the steerable needle. Higher yield stress may be preferred during the bending of the needle so that the needle doesn't yield. A low Young's modulus may allow the needle to bend easier, but the Young's modulus can't be too low that the needle doesn't penetrate tissue. A low damping capacity may also allow the buckle in the needle to translate along the needle without losing energy. These material properties will depend on the intended use of the steerable needle (e.g., the type of tissue being penetrated or the desired curvature of the needle's path), the size and shape of the steerable needle, and the materials used.

In at least one embodiment, the components of the steerable needle may be made of a biocompatible material, such as, for example, stainless steel, shape memory alloys (including nitinol), and other polymers, such as electro-active polymers and some plastics as may be appreciated by any skilled in the art. The components of the steerable needle may each comprise one of more of these materials. Polymer materials are particularly suitable for applications where MRI imaging may be used.

The control mechanism in the base can use conventional controls known in the art for steerable needles, as well as those used for steerable catheters. For example, a control mechanism such as that disclosed in U.S. Patent Application Publication No. 2012/0136381, hereby incorporated by reference, can be used in embodiments of the present disclosure. The control mechanism may comprise, for example, a plunger that can be pushed or pulled to activate the transmission, or a lever or wind-up device (e.g., a twist knob) that causes tension in the transmission. In at least one embodiment, the base can be hand held and controlled by a user (e.g., a surgeon) and the control can be made intuitive. The control mechanism in the base can also be robotic or otherwise automated. The control mechanism may include one or more step-down devices that translate the motion of a user into relatively smaller motions within the steerable needle.

In at least one embodiment, the steerable needle may comprise a payload delivery system. As used herein, the term "payload delivery" refers to the transfer of material (i.e., a "payload") to or from the steerable needle, such as, for example, delivery or retrieval or material located near the tip of the steerable needle or delivery of materials between the base and the shaft of the steerable needle. The payload delivery system may be used, for example, to deliver medications or radioactive seeds, or to remove material, such as a liquid or a tissue for biopsies or other applications. The payload may also comprise a tool or device (e.g., RFA transducer, microwave transducer, illumination source, imager/camera) to be used by the operator. A payload may be located within the needle or even on the exterior of the needle.

According to at least one embodiment, the payload can be carried at or near the tip of the needle (or any other position along the shaft where material is delivered or samples collected) or can be transferred to the desired position after the needle has reached a target site by another medium guided by the needle shaft or can use the path through the tissue created by the needle, such as after the needle has been removed. A needle-tip location for the payload is not a requirement, however, as the payload may be disposed along the needle at a distance from the top.

In at least one embodiment, the needle shaft can have a hollow portion through which the payload may be delivered. The hollow portion of the shaft of the needle may be formed along the entire length of the shaft or a portion of the shaft.

For example, when the payload comprises a medication or a collected sample (e.g., liquid or tissue sample), the payload delivery system may comprise a hollow portion, or compartment; located at or near the distal end of the needle shaft.

Alternatively, the payload delivery system may deliver or retrieve material through the shaft of the steerable needle. According to at least one embodiment, the payload delivery system may comprise a flexible tube. The flexible tube of the payload delivery system may be inserted through the shaft of the needle after the needle has reached its destination or after the needle has been removed (i.e., the flexible tube follows the path created and vacated by the steerable needle), or the flexible tube of the payload delivery system may be inserted with the needle.

The payload delivery system may form an integral part of the steerable (e.g., a hollow portion or compartment within the shaft of the needle itself or a flexible tube or capsule that is contained within a hollow portion of the shaft) or may be a separate component that may be inserted/removed separately from the steerable needle.

It should be understood that the disclosed steerable needles may be used in ablation applications, e.g., radiofrequency ablation, microwave ablation, cryogenic ablation, and the like. The disclosed steerable needles may also be used in ultrasound applications, as well.

As explained elsewhere herein, the disclosed technology is capable of generating arbitrary paths (according to the needs of the user), which stands in contrast to the current state of the art in ablation, which focuses on the ablation of volumes of fixed shape (e.g., roughly spherical volumes) around the fixed location of the ablation transducer. The disclosed technology, however, is capable of ablating volumes of arbitrary shape defined by the path of the needle while moving the needle at a particular rate. Depending on the distance between the needle and the tissue that the user seeks to ablate, this rate may be varied by the user.

EXEMPLARY EMBODIMENTS

Embodiment 1. A steerable needle comprising: a shaft comprising a beam capable of being controllably buckled; a steering head positioned at a distal end of the shaft; a transmission for controlling the orientation of the steering head; and a base positioned at a proximal end of the shaft. The beam may comprise a metallic material, a polymeric material, a ceramic material, and the like. Similarly, the transmission may comprise a metallic material, a polymeric material, a ceramic material, and the like.

It should be understood that either or both of the beam and transmission may comprise a straight beam, an angled beam, an L-beam, a C-beam, a tube, a flattened tube, a tape spring, a rod, and the like. It should also be understood that the transmission and the beam may have the same configuration (e.g., both may be tape springs) or may be of different configurations (e.g., the transmission may be a rod, and the beam may be a tape spring). Although tape springs are considered suitable for use as beams and/or transmissions, there is no requirement that either the beam or transmission be a tape spring.

Embodiment 2. The steerable needle according to embodiment 1, wherein the steering head comprises a beveled tip.

Embodiment 3. The steerable needle according to embodiment 1, wherein the steering head is characterized as conical.

Embodiment 4. The steerable needle according to any of embodiments 1-3, wherein the steering head defines a lumen formed therethrough.

Embodiment 5. The steerable needle according to any of embodiments 1-4, wherein the transmission comprises at least one control linkage, at least one shaft, at least one tape spring, or any combination thereof. It should be understood that any of the foregoing may be moveable in a linear and/or rotatable (twistable) fashion. In this way, a user may use the transmission to impart sliding motion to an aspect of the steerable needle, and may also use the transmission to impart rotational or other twisting motion to an aspect of the steerable needle.

Embodiment 6. The steerable needle according to embodiment 5, wherein the transmission comprises at least two control linkages.

Embodiment 7. The steerable needle according to any of embodiments 1-6, wherein the beam is selected from a straight beam, an angled beam, an L-beam, a C-beam, a rod, or a tape spring.

Embodiment 8. The steerable needle according to any of embodiments 1-7, wherein the beam comprises a flattened tube, and the transmission comprises at least one control linkage contained within said flattened tube.

Embodiment 9. The steerable needle according to any of embodiments 1-8, wherein at least one of the beam and transmission comprises a pre-curved mechanical bias.

Embodiment 10. The steerable needle according to any of embodiments 1-9, wherein the beam comprises at least one edge channel.

Embodiment 11. The steerable needle according to embodiment 10, wherein the transmission comprises at least one control linkage contained within said at least one edge channel.

Embodiment 12. The steerable needle according to any of embodiments 1-11, wherein the beam comprises a first tape spring and wherein the transmission comprises a second tape spring.

Embodiment 13. The steerable needle of embodiment 12, wherein at least one of the first and second tape springs comprises a steering head.

Embodiment 14. The steerable needle according to any of embodiments 12-13, wherein the first tape spring and the second tape spring have pre-curved mechanical biases opposite to one another.

Embodiment 15. The steerable needle according to embodiment 12, wherein the first and second tape springs are oriented such that they form a closed tube.

Embodiment 16. The steerable needle according to embodiment 12, wherein the first and second tape springs are oriented such that a curvature of a first tape spring faces a direction opposite a curvature of a second tape spring.

Embodiment 17. The steerable needle according to embodiments 15-16, wherein the first tape spring and second tape spring are joined at a steering head.

Embodiment 18. The steerable needle according to any of embodiments 1-14, wherein at least one of the shaft and the beam comprises a tubular tape spring.

Embodiment 19. The steerable needle according to any of embodiments 1-18, wherein the steerable needle has a turning radius less than 15 mm, e.g., from about 1 to about 15 mm, or even from about 5 to about 15 mm.

Embodiment 20. The steerable needle according to any of embodiments 1-19, further comprising a payload delivery system within the shaft or on the shaft. A payload delivery system may include, e.g., a tube, a latch, a blister, or other modality configured to deliver a payload, whether solid or fluid.

Embodiment 21. The steerable needle according to embodiment 20, wherein the payload delivery system comprises a hollow portion of the beam.

Embodiment 22. The steerable needle according to embodiment 4, wherein the lumen of the steering head is in fluid communication with a lumen of the beam.

Embodiment 23. The steerable needle according to embodiment 4, wherein the lumen of the steering head is in fluid communication with a fluid source exterior to the steerable needle.

Embodiment 24. The steerable needle according to embodiment 1, wherein the base comprises a robotic controller for controlling the transmission.

Embodiment 25. The steerable needle according to any of embodiments 1-24, further comprising (a) an ablation modality configured to effect ablation within a subject into whom the steerable needle has been inserted, (b) a sensor modality, or both (a) and (b).

Embodiment 26. A steerable needle, comprising: a first tape spring comprising a first steering head adapted for insertion into a living subject, the first steering head located at a distal end of the first tape spring, at least a portion of the first tape spring having a mechanical bias in a first direction; a second tape spring comprising a second steering head adapted for insertion into a living subject, the second steering head located at a distal end of the second tape spring, at least a portion of the second tape spring having a mechanical bias in a second direction opposite the first direction, the first and second tape springs being engaged with one another such that the mechanical bias of the first tape spring at least partially counters the mechanical bias of the second tape spring, the first and second tape springs being further engaged with one another such that upon advancement of the first steering head beyond the second steering head, the first steering head translates in the direction of the mechanical bias of the first tape spring, and the first and second tape springs being further engaged with one another such that upon advancement of the second steering head beyond the first steering head, the second steering head translates in the direction of the mechanical bias of the second tape spring.

Embodiment 27. The steerable needle of embodiment 26, wherein the first tape spring is disposed within the second tape spring.

Embodiment 28. The steerable needle of any of embodiments 35-36, further comprising (a) a transmission configured to exert a force on the first steering head, (b) a transmission configured to exert a force on the second steering head, or both (a) and (b).

Embodiment 29. The steerable needle of any of embodiments 26-28, wherein the second tape spring is configured to conform to a bend in the first tape spring upon advancement of the second steering head in the direction of the distal end of the first tape spring.

Embodiment 30. The steerable needle of any of embodiments 26-29, wherein the first tape spring is configured to conform to a bend in the second tape spring upon advancement of the first steering head in the direction of the distal end of the second tape spring.

Embodiment 31. The steerable needle of any of embodiments 26-30, wherein at least one of the first steering head and the second steering head defines a lumen formed therethrough.

Embodiment 31. The steerable needle of any of embodiments 26-31, wherein the steerable needle comprises a lumen therein.

Embodiment 33. The steerable needle of embodiment 32, wherein the lumen is formed in a conduit disposed within the steerable needle.

Embodiment 34. A steerable needle, comprising: a first tape spring comprising a first steering head adapted for insertion into a living subject, the first steering head located at a distal end of the first tape spring, the first tape spring being disposed within a shaft, the shaft capable of being controllably buckled, and a transmission in mechanical communication with the steering head, the transmission being configured to change an orientation of the steering head, the change of the orientation of the steering head giving rise to a bend in the shaft as the steerable needle is advanced into a subject.

Embodiment 35. The steerable needle of embodiment 34, wherein at least one of the transmission and the shaft having a bias such that the rest-position of the at least one of the transmission and shaft is bent.

Embodiment 36. A steerable needle, comprising: a first shaft comprising a first beam capable of being controllably buckled; a second shaft comprising a second beam capable of being controllably buckled; a steering head, the steering head optionally comprising at least one of the first and second shaft, the orientation of the steering head being capable of being controllably oriented.

Embodiment 37. The steerable needle of embodiment 36, wherein the orientation of the steering head is controllably oriented by a transmission.

Embodiment 38. The steerable needle of embodiment 37, wherein the transmission is in mechanical communication with the steering head, the first shaft, the second shaft, or any combination thereof.

Embodiment 39. The steerable needle of any of embodiments 36-38, wherein the first and second shafts are concave.

Embodiment 40. The steerable needle of embodiment 39, wherein the first and second shafts are assembled so as to define a lumen therebetween.

Embodiment 41. The steerable needle of embodiment 39, wherein the first and second shafts are assembled so as to be concave away from one another.

Embodiment 42. The steerable needle of any of embodiments 36-41, wherein at least one of the first and second shafts has a bias such that the rest-position of the at least one of the first and second shafts is bent.

Embodiment 43. A method, comprising inserting a steerable needle according to any of embodiments 1-42 into a subject.

Embodiment 44. The method of embodiment 43, further effecting at least one bend in the steerable needle and advancing the steerable needle into the subject. A user may advance the steerable needle and then effect the bend, or effect the bend and then advance the steerable needle. A user may also effect a bend in the steerable needle while also advancing the steerable needle in the subject. It should be understood that a user may effect the formation of a second bend, a third bend, a fourth bend, and additional bends in the steerable needle, depending on the user's needs. Put another way, the disclosed steerable needles and related methods are not limited to embodiments wherein only a single bend is formed, as the disclosed technology includes embodiments where a plurality of bends are formed in the steerable needle.

As but one example, the disclosed methods include the steps of: advancing a steerable needle into a subject, effecting a first bend in the steerable needle by changing an orientation of a steering head of the steerable needle so as to effect a bend in a portion of the steerable needle, advancing the steering head of the steerable needle further into the subject, and changing an orientation of a steering head of the steerable needle so as to effect a second bend in a portion of the steerable needle. As shown, a steerable needle may include a first portion that experiences the first bend, and a second portion that is slidably moved along the first portion and the first bend in the first portion, which second portion may then have effected therein a second bend. One such embodiment of the foregoing is shown in FIGS. 8A-8E and FIGS. 9A-9E. (It should be understood that it is not required to advance the steerable needle into the patient in order to effect bends in the steerable needle, as a needle may be actuated and bent without also being inside a patient.)

An alternate embodiment may include, with a steerable needle, effecting a bend in the steerable needle by changing an orientation of a steering head of the steerable needle so as to effect a first bend in a portion of the steerable needle. The needle may be further advanced, and an orientation of the steering head may be changed again so as to effect a second bend in a second portion of the steerable needle.

Embodiment 45. The method of embodiment 44, wherein the bend is effected by exerting a mechanical force on the transmission so as to change an orientation of the steering head, by exerting a magnetic force so as to change an orientation of the steering head, by effecting a thermally-caused change in an orientation of the steering head, or any combination thereof.

Embodiment 46. The method of embodiment 45, wherein the change in orientation is characterized as movement in one plane.

Embodiment 47. The method of embodiment 45, wherein the change in orientation is characterized as rotational.

Embodiment 48. The method of any of embodiments 43-47, further comprising advancing at least a portion of the steerable needle into the subject so as to create a curved pathway within the subject.

Embodiment 49. The method of any of embodiments 43-48, further comprising withdrawing a material from the subject through the steerable needle.

Embodiment 50. The method of any of embodiments 43-49, further comprising delivering a material to the subject through the steerable needle.

Embodiment 51. The method of any of embodiments 43-50, further comprising effecting ablation within the subject, the ablation being effect by an ablation modality of the steerable needle.

In summary, the disclosed technology provides distinct advantages over existing approaches. Further, the disclosed steerable needles may be integrated into a large variety of processes. For example, the disclosed technology is suitable for use with microwave ablation (MWA), radio frequency ablation (RFA), direct injection, MRI, chemo-electrical, cryogenic applications, aspiration, robotic or automated surgical platforms, and the like.

The invention has been described in detail, with particular reference to certain preferred embodiments thereof, but it will be understood that variations and modifications can be effected within the scope of the invention as described above, by a person of ordinary skill in the art, without departing from the scope of the invention.

What is claimed is:

1. A steerable needle, comprising:
    a first tape spring comprising a first steering head adapted for insertion into a living subject, the first steering head located at a distal end of the first tape spring, at least a portion of the first tape spring having a mechanical bias in a first direction;
    a second tape spring comprising a second steering head adapted for insertion into a living subject, the second steering head located at a distal end of the second tape spring at least a portion of the second tape spring having a mechanical bias in a second direction opposite the first direction, wherein:
        the first and second tape springs are engaged with one another such that the mechanical bias of the first tape spring counters the mechanical bias of the second tape spring;
        the first and second tape springs are further engaged with one another such that upon advancement of the first steering head beyond the second steering head, the first steering head translates in the direction of the mechanical bias of the first tape spring, and the first and second tape springs are further engaged with one another such that upon advancement of the second steering head beyond the first steering head, the second steering head translates in the direction of the mechanical bias of the second tape spring.

2. The steerable needle of claim 1, wherein the first tape spring is disposed within the second tape spring.

3. The steerable needle of any of claim 1, further comprising:
    (a) a transmission configured to exert a force on the first steering head;
    (b) a transmission configured to exert a force on the second steering head; or
    both (a) and (b).

4. The steerable needle of claim 1, wherein the second tape spring is configured to conform to a bend in the first tape spring upon advancement of the second steering head in the direction of the distal end of the first tape spring.

5. The steerable needle of claim 1, wherein the first tape spring is configured to conform to a bend in the second tape spring upon advancement of the first steering head in the direction of the distal end of the second tape spring.

6. The steerable needle of claim 1, wherein at least one of the first steering head and the second steering head defines a lumen formed therethrough.

7. The steerable needle of claim 1, wherein the steerable needle comprises a lumen therein.

8. The steerable needle of claim 7, wherein the lumen is formed in a conduit disposed within the steerable needle.

9. The steerable needle according to claim 1, wherein the first steering head, the second steering head, or both, comprise a beveled tip.

10. The steerable needle according to claim 1, wherein the first, steering head, the second steering head, or both, are characterized as conical.

11. The steerable needle according to claim 1, wherein the first steering head, the second steering head, or both, define a lumen formed therethrough.

12. The steerable needle according to claim 1, wherein the first and second tape springs are oriented such that they form a closed tube.

13. The steerable needle according to claim 1, wherein the first and second tape springs are oriented such that a curvature of a first tape spring faces a direction opposite a curvature of a second tape spring.

14. The steerable needle according to claim 1, wherein the steerable needle has a turning radius less than 15 mm.

* * * * *

UNITED STATES PATENT AND TRADEMARK OFFICE
CERTIFICATE OF CORRECTION

| | |
|---|---|
| PATENT NO. | : 11,950,805 B2 |
| APPLICATION NO. | : 18/191286 |
| DATED | : April 9, 2024 |
| INVENTOR(S) | : Mark Yim |

It is certified that error appears in the above-identified patent and that said Letters Patent is hereby corrected as shown below:

In the Specification

Under Column no. 8, Line no. 5, Replace:
"mm,"
With:
--35 mm,--

Under Column no. 8, Line no. 9, Replace:
"mm,"
With:
--15 mm,--

Under Column no. 8, Line no. 31, Replace:
"that that"
With:
--that--

Under Column no. 13, Line no. 5, Replace:
"4'T"
With:
--47'--

Under Column no. 14, Line no. 56, Replace:
"reversed"
With:
--reversed.--

Signed and Sealed this
Nineteenth Day of August, 2025

Coke Morgan Stewart
*Acting Director of the United States Patent and Trademark Office*

CERTIFICATE OF CORRECTION (continued)
U.S. Pat. No. 11,950,805 B2

In the Claims

Under Column no. 22, Claim 3, Line no. 8, Replace:
"of any of claim"
With:
--of claim--

Under Column no. 22, Claim 9, Line no. 32, Replace:
"according to"
With:
--of--

Under Column no. 22, Claim 10, Line no. 35, Replace:
"according to"
With:
--of--

Under Column no. 22, Claim 10, Line no. 36, Replace:
"first,"
With:
--first--

Under Column no. 22, Claim 11, Line no. 38, Replace:
"according to"
With:
--of--

Under Column no. 22, Claim 12, Line no. 41, Replace:
"according to"
With:
--of--

Under Column no. 22, Claim 13, Line no. 44, Replace:
"according to"
With:
--of--

Under Column no. 22, Claim 14, Line no. 48, Replace:
"according to"
With:
--of--